US006312696B1

(12) United States Patent
Tsuzaki et al.

(10) Patent No.: US 6,312,696 B1
(45) Date of Patent: Nov. 6, 2001

(54) ANTIGENIC PROTEIN ORIGINATING IN INFECTIOUS LARYNGOTRACHEITIS VIRUS

(75) Inventors: Yoshinari Tsuzaki; Takashi Okuda, both of Kawasaki (JP)

(73) Assignee: Nippon Zeon Co., LTD, Tokyo (JP)

( * ) Notice: Subject to any disclaimer, the term of this patent is extended or adjusted under 35 U.S.C. 154(b) by 0 days.

(21) Appl. No.: 09/242,632

(22) PCT Filed: Aug. 21, 1997

(86) PCT No.: PCT/JP97/02912

§ 371 Date: Feb. 19, 1999

§ 102(e) Date: Feb. 19, 1999

(87) PCT Pub. No.: WO98/07866

PCT Pub. Date: Feb. 26, 1998

(30) Foreign Application Priority Data

Aug. 21, 1996 (JP) ........................ 8-238580

(51) Int. Cl.[7] ........................ A61K 39/12; A61K 39/265; C12N 7/04; C12N 1/20; C07K 1/00

(52) U.S. Cl. ........................ 424/186.1; 424/204.1; 424/199.1; 424/816; 424/252.3; 435/236; 435/235.1; 435/320.1; 530/350

(58) Field of Search ........................ 424/93.2, 186.1, 424/202.1, 199.1, 232.1, 229.1, 816; 435/5, 6, 252.3, 325, 235.1, 236, 320.1, 148; 436/504; 514/12; 530/324, 350; 536/23.72

(56) References Cited

PUBLICATIONS

Jennifer J. York et al; Archives of Virology; vol. 115, pp. 147–162, 1990.

Kritaya Kongsuwan et al; Virus Research; vol. 29, pp. 125–140, 1993.

Gary R. Whittaker et al; Journal of General Virology; vol. 73, pp. 2933–2940, 1992.

*Primary Examiner*—Mary E. Mosher
*Assistant Examiner*—Shanon Foley
(74) *Attorney, Agent, or Firm*—Armstrong, Westerman, Hattori, McLeland & Naughton, LLP

(57) ABSTRACT

The present invention discloses a DNA molecule that encodes a polypeptide that has the amino acid sequence described in SEQ ID No. 2 or an amino acid sequence that is at least 80% homologous with said amino acid sequence, a recombinant containing said DNA molecule, and a vaccine having for its active ingredient said recombinant.

34 Claims, 10 Drawing Sheets

E: EcoRI, H: HindIII, B: BamHI, G: BglII, S: SmaI
K: KpnI, Ava: AvaII, Sac: SacI, X: XbaI

ANTIGENIC PROTEIN ORIGINATING IN INFECTIOUS LARYNGOTRACHEITIS VIRUS

FIELD OF THE INVENTION

The present invention relates to an antigen protein derived from infectious laryngotracheitis virus, its gene, a recombinant gene comprising that gene, and a vaccine for infectious laryngotracheitis having as its active ingredient said recombinant gene or the antigen protein.

RELATED ART

Infectious laryngotracheitis occurs due to infection by infectious laryngotracheitis virus (abbreviated as ILTV). ILTV infects chickens, pheasants, peacocks, turkeys and other fowls. Characteristics of its occurrence in chickens include respiratory organ symptoms, fever, reduced appetite and so forth. Intense cough and expectoration of sputum are observed. In addition; in egg-laying chickens, the rate at which eggs are laid decreases about 4 days after onset, and about 1 month is required for egg-laying to return to a normal level. Moreover, an increases in mortality rates due to mixed infection with other pathogens have also been reported, thus causing a tremendous economic loss in the poultry industry.

Dried live vaccines and frozen live vaccines from attenuated vaccine strains have conventionally been used for prevention of infectious laryngotracheitis. However, their immune effects vary considerablly depending on the breeding environment, breeding density, inoculation method and so forth. Moreover, inoculation of vaccine causes some symptoms in the respiratory system, and there is the risk of illness if errors are made in an administration manner or inoculated amount. In addition, there are also reports of onset of illness due to recovery of pathogenicity from the vaccine strain in certain geographical regions, thus creating the need for the development of a safe and effective vaccine.

ILTV is a type of Herpes virus. Its virus genome is composed of double-stranded DNA of approximately 160,000 base pairs. At present, very few genes are identified, and the only ones that are known are thymidine kinase gene (Griffin, et al., J. Gen. Virol., Vol. 71, p. 841, 1990), gp60 gene (Kongsuwan, et al., Virus Genes, Vol. 7, p. 297–303, 1993), capsid p40 gene (Griffin, Nucl. Acids Res., Vol. 18, p. 3664, 1990), glycoprotein B (gB) gene (Poulsen, et al., Virus Genes, Vol. 5, p. 335–347, 1991), glycoprotein C (gC) gene (Kingsley, et al., Virology, Vol. 203, p. 336–343, 1994), and RR2 gene (Griffin, J. Gen. Virol., Vol. 70, p. 3085–3089, 1989). In addition, several homologous genes are known to exist between each strain of Herpes virus. For example, there is an each homologous gene of gB in Herpes simplex virus (HSV-1), Marek's disease virus (MDV), Bovine Herpes virus (BHV), equine Herpes virus (EHV), cytomegalovirus (CMV) and so forth. However, although homologous genes are also reported in EHV with respect to UL32 gene of HSV-1 (Whittaker, et al., J. Gen. Virol., Vol. 73, p. 2933, 1992), there are as of yet no known homologous genes for ILTV. Moreover, the use of these genes for vaccines is also not known.

DISCLOSURE OF THE INVENTION

As a result of earnest studies to obtain a gene that encodes a novel antigen protein of ILTV considering the above-mentioned teaching, the inventors of the present invention found an ILTV homologous gene to UL32 gene of HSV-1, thereby leading to completion of the present invention.

According to the present invention, a polypeptide (referred to as UL32h polypeptide) is provided that has an amino acid sequence that is at least 80% homologous with the amino acid sequence described in SEQ ID No. 2.

In addition, the present invention provides a DNA molecule that encodes a protein having an amino acid sequence that is modified by deletion, addition and/or substitution by other amino acids of one or a plurality of amino acids in the amino acid sequence described in SEQ ID No. 2, and maintains the immunogenicity of infectious laryngotracheitis virus.

Moreover, the present invention provides a DNA molecule that encodes a protein that hybridizes with a nucleic acid having the nucleotide sequence described in SEQ ID No. 1 under conditions of 42° C., 2% skim milk, 6-fold concentrated SSC (6×SSC; pH 7.0) and 0.1% SDS, and still has the immunogenicity of infectious laryngotracheitis virus.

In addition, the present invention provides a recombinant DNA molecule comprising the above-mentioned DNA and at least one additional DNA sequence.

In addition, the present invention provides a recombinant vector that comprises the DNA sequence of any of the above-mentioned DNA molecules.

Moreover, the present invention provides a transformant host having any of the above-mentioned DNA molecules.

Moreover, the present invention provides a recombinant virus having any of the above-mentioned DNA molecules.

Moreover, the present invention provides a polypeptide having an amino acid sequence that is at least 80% homologous with the amino acid sequence described in SEQ ID No. 2.

Moreover, the present invention provides a protein having an amino acid sequence that is modified by deletion, addition and/or substitution by other amino acids of one or a plurality of amino acids in the amino acid sequence described in SEQ ID No. 2, and still maintains the immunogenicity of infectious laryngotracheitis virus.

Moreover, the present invention provides a protein encoded by DNA that hybridizes with a nucleic acid having the nucleotide sequence described in SEQ ID No. 1 under conditions of 42° C., 2% skim milk, 6-fold concentrated SSC (6×SSC; pH 7.0) and 0.1% SDS, and has the immunogenicity of infectious laryngotracheitis virus.

Moreover, the present invention provides a live vaccine for infectious laryngotracheitis virus having for its active ingredient the above-mentioned recombinant virus.

Moreover, the present invention provides a vaccine for infectious laryngotracheitis virus having for its active ingredient any of the above-mentioned polypeptides or its pharmacologically acceptable carrier.

EMBODIMENT FOR CARRYING OUT THE INVENTION

DNA Molecule

Figure 1:
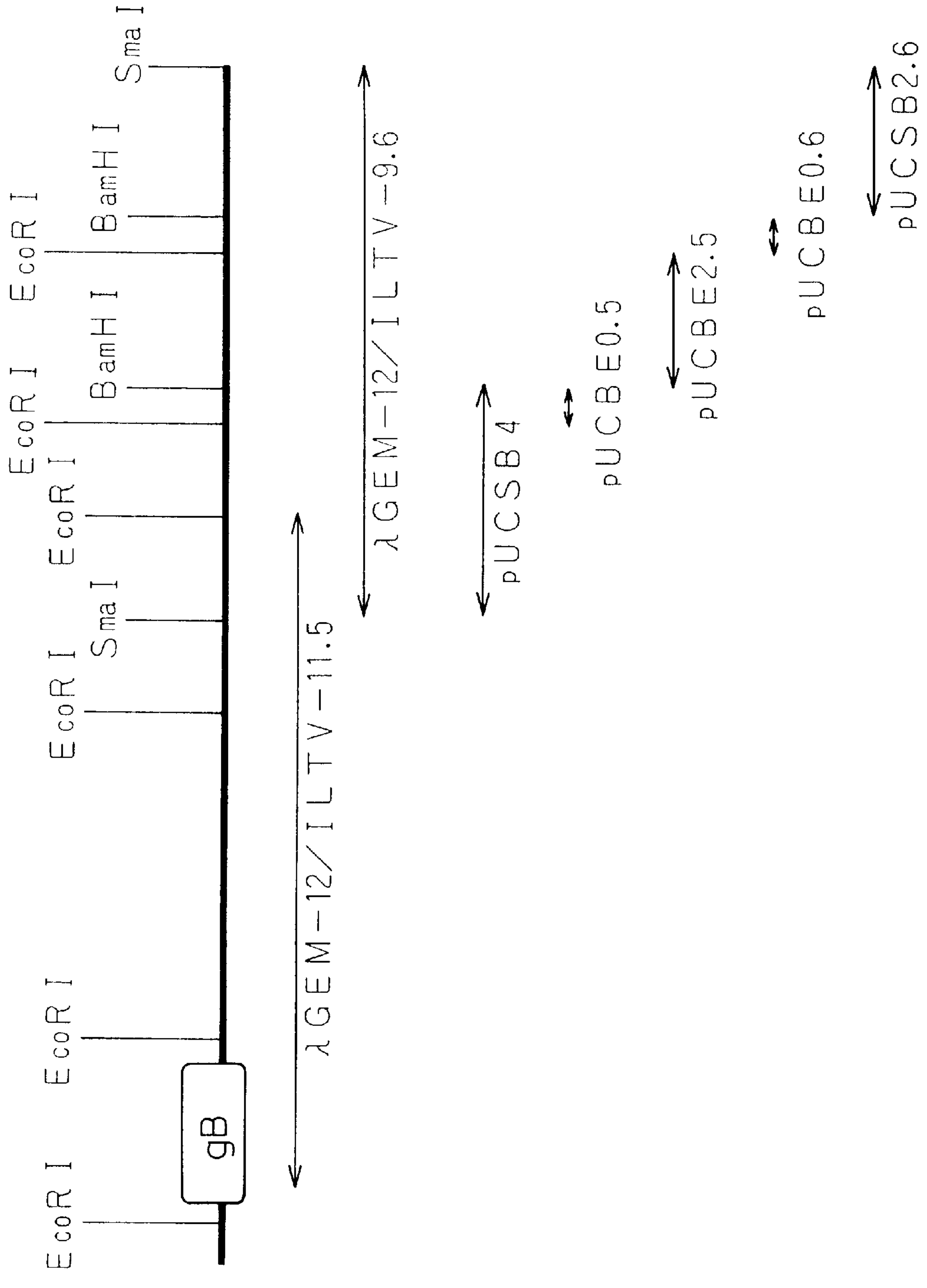
FIG. 1 is a diagram showing the restriction enzyme cleavage map of a DNA fragment originating in ILTV genome.

The DNA molecule of the present invention is a gene that encodes an antigen polypeptide having the amino acid sequence indicated in SEQ ID No. 2, or that which encodes an amino acid sequence that is at least 80%, preferably at least 90%, and more preferably at least 95%, homologous with said gene, a specific example of which is the nucleotide sequence of SEQ ID No. 1.

In addition, the DNA molecule of the present invention is a DNA molecule that encodes a protein having an amino acid sequence that is modified by deletion, addition and/or substitution by other amino acids or one or a plurality of amino acids in the amino acid sequence described in SEQ ID No. 2, and still maintains the immunogenicity of infectious laryngotracheitis virus; and includes a DNA molecule that encodes a protein that hybridizes with a nucleic acid having the nucleotide sequence described in SEQ ID No. 1 under conditions of 42° C., 2% skim milk, 6-fold concentrated SSC (6×SSC; pH 7.0) and 0.1% SDS.

Homology referred to in the present invention refers entirely to that which is calculated using the sequence database software "DNASIS" (sold by: Takara Shuzo, manufactured by: Hitachi Software Engineering) using the algorithm of Lipman and Pearson (Science, 227, 1435, 1985).

Any strain may be used for cloning of the DNA molecule of the present invention (UL32h gene), examples of which include strain NS-175 (strain no. VA0204 of the Livestock Hygiene Strain Catalog, Animal Biological Preparation Association), strain CE (Sachida, Azabu Veterinary College Research Report, 31, p. 133–202, 1976), strain SA-2 (Johnson, et al., Arch. Virol., Vol. 119, p. 181–198, 1991), and strain 632 (Keeler, et al., Avian Diseases, Vol. 35, p. 920–929, 1991).

The gene that encodes the polypeptide described in SEQ ID No. 1 of the present invention (UL32h gene) is homologous with the UL32 gene of HSV-1. Moreover, the UL32 gene of HSV-1 of HSV-1 is located on the internal repeat side approximately 15 Kbp from gB gene in the long unique region, and the gene configuration between Herpes virus species is extremely similar (Roizman and Sears, Virology, Second Edition, Chapter 65, 1795–1841, 1990). Based on this, in terms of the ILTV genome as well, UL32h gene is predicted to be present on the internal repeat side from gB gene.

According to the above reasons, in order to obtain a DNA fragment containing the UL32h gene of ILTV, gene-walking method was performed by preparing the λGEM-12 library of the strain NS-175 genome of ILTV, selecting a clone that hybridizes with the gB gene of ILTV from this library, and additionally selecting a clone that hybridizes to the internal repeat side fragment of ILTV genomic DNA having that clone, followed by repeating this procedure.

The sequence of the ILTV genomic DNA fragment obtained in this manner was analyzed, and the amino acid sequence predicted from that sequence was compared with the amino acid sequence of UL32 polypeptide of HSV-1. As a result, an open reading frame was obtained that encodes polypeptide homologous to the amino acid sequence of UL32 polypeptide of HSV-1. That DNA fragment and the estimated amino acid sequence are shown in SEQ ID No. 2.

Recombinant DNA Molecule

The recombinant DNA molecule-of the present invention comprises the above-mentioned DNA molecule of the present invention (for example, UL32h gene) and at least one type of additional DNA sequence ligated by gene manipulation. The additional DNA sequence referred to here is a sequence that is not linked with the UL32h gene of ILTV in nature, specific examples of which include a marker gene such as lacZ gene, gB gene of ILTV, gI gene of MDV, gE gene of MDV and other antigen genes. In addition, any method may be used for linking the additional DNA sequence provided it does not inhibit expression of each gene. The additional DNA sequence should be linked using DNA ligase in accordance with routine methods either directly or by means of a linker sequence after digesting with a suitable restrictase.

Recombinant Vector

The recombinant vector of the present invention is a recombinant vector containing at least the above-mentioned DNA molecule or recombinant DNA molecule of the present invention, and is inserted with a promoter or marker and so forth to be described later.

A vector that recombines these DNA molecules is arbitrarily selected from plasmids, cosmids and phages typically used as vectors. The DNA molecules should be inserted in accordance with routine methods by treating plasmids such as pBR322, pBR325, pUC7, pUC8, pUC18 or pUCl9, phages such as λ-phage or M13 phage, or cosmids such as pHC79 with a suitable restriction enzyme. In addition, in the case of using this recombinant vector for preparing a recombinant virus, a DNA molecule is inserted after recombining a non-essential region like that described later.

Recombinant Virus

The recombinant virus of the present invention contains the above-mentioned DNA molecule (for example, UL32h gene) or recombinant DNA molecule as antigen gene, and is constructed by inserting one of these DNA molecules into a region that is not essential for propagation of the parent virus in accordance with routine methods such as homologous recombination.

In addition, a promoter or marker gene can also be contained in addition to DNA molecules as necessary.

Parent Virus

The parent virus used in the present invention is a virus into which the DNA molecule of the present invention is inserted, and there are no particular limitations on its type. Specific examples of such viruses include avipox virus (APV) such as fowlpox virus (FPV), equilpox virus, turkey pox virus, pigeon pox virus; baculoriruses such as *Autographa californica, TrichoDlusia ni, Rachiplusia ou, Galleria mellonella, Bombvx mori*; and turkey Herpes virus, etc. Viruses that infect fowls are particularly favorable for production of live vaccines, and avipox viruses are particularly favorable, specific examples of which include ATCC VR-251, ATCC VR-250, ATCC VR-229, ATCC VR-249, ATCC VR-288, Nishigahara strain, Shisui strain, CEVA strain, FPV in the narrow sense such as viruses originating in CEVA vaccine strains that form a large plaque when infecting CEF (chicken embryo fibroblast) cells, and viruses similar to FPV in the narrow sense that are used as chickenpox live vaccines such as pigeon pox virus strain NP (chicken embryonic pigeon pox Nakan strain). These can be easily acquired since they are either commercially available or are deposited at official institutions.

Non-Essential Region

The non-essential region used in the present invention is a DNA region that is not essential for propagation of the above-mentioned virus (parent virus) or a region that allows homologous recombination with it. Examples of regions that can be used include the polyhedrin gene region of baculovirus, the TK gene region of viruses belonging to the pox virus family, and the non-essential region of the avipox virus described in Japanese Unexamined Patent Publication No. 1-168279. Specific examples of non-essential regions of avipox viruses include the EcoRI fragment (7.3 Kbp), EcoRI-HindIII fragment (approx. 5.0 Kbp), BamHI fragment (approx. 4.0 Kbp) and HindIII fragment (approx. 5.2 Kbp) of the pigeon pox virus strain NP DNA described in the above-mentioned publication, the TK gene region of quail pox virus, the TK gene region of turkey pox virus, or regions that cause homologous recombination with them.

Vector Containing a Virus Non-Essential Region

The vector containing a virus non-essential region used in construction of a vector for virus recombination used in the present invention may be that which is similar to the above-mentioned recombinant vector, and it is inserted into the above-mentioned virus non-essential region in accordance with routine methods by treating the vector with a suitable restriction enzyme.

Antigen Gene

The antigen gene inserted into a virus in the present invention may not only be the DNA molecule that encodes the amino acid sequence indicated in SEQ ID No. 2 (a specific example of which is that having the nucleotide sequence described in SEQ ID No. 1), but also its fragment, a gene or a part of gene and modified one, which does not impair the ability to induce a defense immune reaction. Such a modified antigen protein in which a portion of such a fragment or sequence has an amino acid sequence that has been altered with respect to the amino acid sequence described in SEQ ID No. 2, and is also considered to give a substantially equivalent immune reaction in a host. Gene modification is that in which at least one amino acid has been artificially modified (including substitution, insertion and deletion) by routine methods such as the site-specific mutation induction methods described in Nucleic Acid Research, Vol. 10, No. 20, p. 6487–6500 (1982) or Japanese Examined Patent Publication No. 6-16709, and is preferably at least 80%, more preferably at least 90%, and still more preferably at least 95% homologous with the amino acid sequence described in SEQ ID No. 2.

The antigen gene of the present invention may also be that which comprises a DNA molecule that hybridizes with a nucleic acid having the nucleotide sequence described in SEQ ID No. 1 under conditions of 42° C., 2% skim milk, 6-fold concentrated SSC (6×SSC; pH 7.0) and 0.1% SDS, and encodes a protein having the immunogenicity of infectious laryngotracheitis virus. The DNA referred to here that hybridizes with a nucleic acid having the nucleotide sequence of SEQ ID No. 1 is preferably that which originates in nature, an example of which is that which is derived from infectious laryngotracheitis virus.

This gene may be inserted into one region or two or more different regions of the virus genome. Moreover, it can also be recombinated with gene or its fragment encoding a protein, such as lacZ gene, gB or gC gene of ILTV; or gB, gC, gD, gH, gI or gE gene of MDV.

Recombination Vector

The vector used for virus recombination in the present invention contains a virus non-essential region into which has been inserted at least the DNA molecule of the present invention and a promoter that controls it. The above-mentioned antigen gene and a promoter that controls it should be inserted into virus non-essential region of the above-mentioned vector that contains a virus non-essential region. In addition, a fragment that contains a virus non-essential region into which has been inserted an antigen gene originating in such a vector and a promoter may also be recombinated in another vector. Moreover, a marker gene such as lacZ gene of *E. coli* and a promoter that controls it may also be recombined for purification of recombinant virus and so forth.

Promoter

There are no particular limitations on the promoter used here provided it functions as a promoter in a recombinant virus-infected host. Examples of promoters that can be used include the promoter of vaccinia virus gene encoding 7.5 K polypeptide, the promoter of vaccinia virus gene encoding 11 K polypeptide, the promoter of vaccinia virus encoding thymidine kinase, the polyhedrin promoter of baculovirus, and the SV40 promoter of turkey Herpes virus, modified promoters, such as those in which a portion has been deleted, provided they still function as promoters, and synthetic promoters that function as promoters in viruses belonging to the pox virus family with reference to the document of Moss, et al. (J. Mol. Biol., Vol. 210, p. 749–776, p. 771–784, 1989).

Recombinant Virus Preparation Method

There are no particular limitations on the recombinant virus preparation method, and preparation can be performed in accordance with conventional methods. In other words, homologous recombination occurs between a vector and viral genomic DNA in infected cells resulting in the construction of a recombinant virus as a result of a recombination vector being introduced into cells pre-infected with virus by, for example, calcium phosphate coprecipitation. The resulting recombinant virus is infected into host cells cultured in a suitable medium, and the plaque that grows is selected as a candidate for the target recombinant virus. This candidate strain is then purified by hybridization using a recombinated antigen gene as a probe, or by selecting that expressed by a recombinated marker gene with an antigen gene. The candidate strain should then be confirmed to be the target recombinant virus by using immunoassay using antibody to antigen encoded by the recombinated antigen gene. For example, in the case of a recombinant virus in which lacZ gene is recombinated as the marker gene, β-galactosidase is expressed and a blue plaque is formed in the presence of one of its substrates, Bluo-Gel (Gibco-BRL).

There are no particular limitations on the host cells provided the virus used is able to infect and propagate in those cells. Examples of host cells that can be used include CEF cells and growing chicken egg chlorioallantoic cells in the case of using FPV, *Spodoptera frugiperda* cells in the case of using baculovirus, and duck embryo fibroblasts in the case of using turkey Herpes virus.

Transformant

The transformant of the present invention refers to cells or microorganisms transformed by a DNA molecule or recombinant DNA molecule of the present invention, or by an expression vector containing such a DNA molecule.

There are no particular limitations on vectors for constructing an expression recombinant vector having a DNA molecule or recombinant DNA molecule of the present invention, and examples of such vectors include plasmids pUC8, pUC9, pUC10, pUC11, pUC18, pUC19, pBR322, pBR325, pBR327, pDR540 and pDR720, as well as phages such as λgt11, λgt10, λEMBL3, λEMBL4 and Charon4A.

The method for inserting a DNA molecule or recombinant DNA molecule of the present invention into such a vector to form an expression recombinant vector may be in accordance with conventional methods, for example, after cleaving a vector with a restriction enzyme, the above-mentioned gene is ligated directly under the control of a promoter that functions in the host. Examples of promoters that are used include lac promoter-operator, trp promoter, tac promoter, lpp promoter, PL promoter, amyE promoter, Ga17 promoter, PGK promoter and ADH promoter.

In terms of preparing a recombinant vector for expressing UL32h polypeptide derived from ILTV, a subcloning method in which the above-mentioned DNA molecule or recombinant DNA molecule is temporarily inserted into a suitable vector to prepare a recombinant vector is a widely known method among persons with ordinary skill in the art, and these subcloned genes can be cut out with a suitable restriction enzyme and ligated to one of the above-mentioned promoters to prepare an expression vector that is able to produce protein. There are no particular limitations on the vectors that can be used in the above-mentioned subcloning, examples of which include plasmids such as pUC8, pUC9, pUC10, pUC11, pUC18, pUC19, pBR322, pBR325, pBR327, pDR540, pDR720, pUB110, pIJ702, YEp13, YEp24, YCp19, YCp50, pAC373 and pACTM1.

A microorganism can be obtained that has the ability to produce a fusion protein containing UL32h amino acid sequence derived from ILTV or its polypeptide having antigenicity by transforming various suitable hosts using the resulting expression vector.

The host used here can be selected in consideration of suitability for the expression vector, stability of the product and so forth, and may be either procaryotic or eukaryotic cells, specific examples of which include Escherichia species (e.g., *Escherichia coli*), Salmonella species (e.g., *Salmonella typhimurium*), Actinomycetes, yeasts, insect cells, avian cells and human cells. Hosts transformed by introduction of a suitable expression vector can be cultured and propagated under culturing conditions widely known among persons with ordinary skill in the art.

In addition, in the production of protein, conditions can be selected that induce promoter action, specific examples of which include the addition of isopropylthio-β-D-galactopyranoside to a suitable amount of culture medium in the case of, for example, lac promoter-operator.

The manufacturing of infectious laryngotracheitis virus vaccine using a transformed host obtained in this manner may be performed in accordance with conventional methods. For example, the culturing of this host may be performed under conditions normally used for culturing microorganisms such as, in the case of *E. coli*, using LB culture medium at 37° C. under aerophilic conditions.

Antigen Polypeptide

The antigen polypeptide of the present invention (for example, UL32h polypeptide) is encoded by the above-mentioned DNA molecule of the present invention (for example, UL32h gene). More specifically, it has the amino acid sequence described in SEQ ID No. 2, or an amino acid sequence which is at least 80%, preferably at least 90%, and more preferably at least 95% homologous with said sequence.

In addition, the antigen polypeptide of the present invention may be an analogue of the polypeptides having these sequences. The analogue referred to here is sufficiently homologous relative to UL32h polypeptide having the amino acid sequence of SEQ ID No. 2 so that it induces a defense immune reaction in a host in the case of being administered, and may be a variant in which the amino terminal, carboxy terminal, central portion or other portion of the amino acids of the above-mentioned sequence is missing, or a variant in which these missing portions are combined. In addition, the analogue may also be a variant in which one or more amino acids is substituted by another amino acid, or may be a combination of these. Sequence alteration is that in which one or more amino acids is modified (including substitution, insertion and deletion) artificially by conventional methods, examples of which include the site-specific mutagenization methods described in Nucleic Acid Research, Vol. 10, No. 20, p. 6487–6500 (1982) or Japanese Examined Patent Publication No. 6-16709, and is at least 80%, preferably at least 90% and more preferably at least 95% homologous relative to the amino acid sequence described in SEQ ID No. 2.

The polypeptide of the present invention may also be a protein that is encoded by DNA that hybridizes with the nucleic acid having the nucleotide sequence described in SEQ ID No. 1 under conditions of 42° C., 2% skim milk, 6-fold concentrated SSC (6×SSC; pH 7.0) and 0.1% SDS, and has the immunogenicity of infectious laryngotracheitis virus. The DNA referred to here that hybridizes with the nucleic acid having the nucleotide sequence described in SEQ ID No. 1 is preferably or natural origin and is, for example, that which is derived from infectious laryngotracheitis virus.

This type of antigen polypeptide can be produced by culturing the above-mentioned transformant of the present invention. In addition, it can also be produced by culturing the above-mentioned recombinant virus of the present invention in suitable host cells.

The produced antigen polypeptide can be isolated and purified in accordance with the description of Methods in Enzymology, Vol. 182 ("Guide to Protein Purification" Murry P. Deutscher, ed., Academic Press pub.).

The antigen polypeptide obtained in this manner is diluted in accordance with routine methods, or is mixed with a suitable adjuvant and so forth to enable it to be used as a component vaccine. Examples of adjuvants used include Freund's complete adjuvant, Freund's incomplete adjuvant, alum and aracel. Although there are no particular limitations on the mixing ratio with adjuvant, the mixing ratio is normally 1:1. In the case of using as a component vaccine, in chickens, the component vaccine should normally be administered at 0.01 μg or more per body, and there is no particular upper limit on the dosage provided acute toxicity is not exhibited. In addition to administering by subcutaneous, intravenous, intramuscular or intraperitoneal injection, the component vaccine can be used for immunization by spraying or by administering in drinking water and so forth.

Moreover, this UL32h polypeptide can also be used as a diagnostic agent for infectious laryngotracheitis.

Live Vaccine

The live vaccine of the present invention is a vaccine composed of the recombinant virus of the present invention. Namely, in addition to using a recombinant virus into which only the antigen gene disclosed in the present invention is inserted, the combined use of this recombinant virus with a recombinant virus into which another antigen gene, such as gBh gene derived from ILTV, gB gene of MDV or HN gene and F gene of NDV, has been inserted, or a recombinant virus into which another antigen gene, such as gBh gene derived from ILTV, gB gene of MDV or HN gene and F gene of NDV, has been inserted in combination with the antigen gene of the present invention may also be used. Synergistic immunogenicity improving effects are obtained by combined use of the antigen gene of the present invention with another antigen gene. In addition, pharmacologically acceptable carriers, such as physiological saline, may also be contained in addition to the recombinant virus.

There are no particular limitations on the preparation method of the vaccine of the present invention. For example, the recombinant virus of the present invention is infected into cells that allow the virus used in the present invention to grow, followed by culturing the infected cells until the recombinant virus propagates. Later, the cells are recovered and homogenized. This cell homogenate is then centrifuged and separated into a centrifuged supernatant that contains cell-free recombinant virus of a high titer, and sediment. The centrifuged supernatant, which contains cell culture medium and recombinant virus but is substantially free of host cells, can be used as the vaccine of the present invention. In addition, it may also be used after reconstituting with a pharmacologically acceptable carrier such as physiological saline. Moreover, the centrifuged supernatant can be freeze-dried and used as a freeze-dried vaccine.

The vaccine of the present invention may be administered by any method provided the method allows the recombinant virus in the vaccine to infect and bring about defense immunity in domestic fowl. For example, domestic fowl may be inoculated with vaccine by scratching the skin, or by administering vaccine subcutaneously to domestic fowl using a syringe needle or other instrument. In addition, the vaccine can be suspended in domestic fowl drinking water or mixed into solid feed to inoculate orally. Moreover, methods in which vaccine is inhaled by using an aerosol or spray, intravenous inoculation methods, intramuscular inoculation methods and intraperitoneal inoculation methods can also be used.

The inoculated amount is normally $10^3$ to $10^6$ pfu (plaque forming units) per fowl in the case of, for example, inoculating chickens with recombinant avipox virus. In the case of injection, this amount may be diluted to about 0.1 ml with a pharmacologically acceptable liquid such as physiological saline.

Although there are no limitations on the time of inoculation, it is preferable that inoculation be made at age 14 days or later in the same manner as existing vaccines based on the objective of providing immunity.

Vaccines of the present invention that have for their active ingredient recombinant avipox virus are cell-free vaccines, and can be stored and used under ordinary conditions. Consequently, storage in liquid nitrogen, handling, inoculation and other bothersome procedures required in the case of existing cell associated vaccines can be reduced. For example, freeze-drying of the recombinant avipox virus of the present invention allows it to be stored for a long time, handled and transported at room temperature (about 20–22° C.). Since the cell-free recombinant avipox virus in this vaccine can be stored even when freeze-dried, for example, a suspension of recombinant avipox virus can be stored by freezing at −20° C. to −70° C.

EXAMPLES

Example 1

Gene Walking of ILTV Strain NS-175 Genomic DNA (see FIG. 1)

ILTV strain NS-175 (purchased from the Animal Biological Pharmaceutical Association) was inoculated into growing chicken egg chlorioallantoic membrane, and ILTV genomic DNA was prepared in accordance with the method of Pignatti, et al. (Virology, Vol. 93, p 260–264, 1979) from the chlorioallantoic fruid recovered 4 days later. The resulting genomic DNA was partially digested with restriction enzyme Sau3AI, and after ligating into λGEM-12 half site arms (Promega), in vitro packaging was performed to prepare a λGEM-12 library.

To begin with, a λ phage inserted with various fragments of ILTV genomic DNA was infected into *E. coli* and plaques were formed on agar medium. Next, the plaques were blotted onto a 0.22 μm pore nitrocellulose filter and plaque hybridization was performed using the gBh gene of ILTV as a probe to obtain a λGEM-12/ILTV-11.5 clone containing approximately 11.5 Kbp of DNA. The DNA inserted into this clone was confirmed from restriction enzyme mapping to be extending approximately 10 Kbp from the N-terminal of gBh gene (FIG. 1). UL32 gene is known to be present at a location approximately 10 Kbp from the N-terminal of gB gene in HSV-1 belonging to Herpes virus family in the same manner as ILTV (Mcgeoch, et al., J. Gen. Virol., Vol. 69, p. 1531–1574, 1988). Based on this, UL32h gene is predicted to be present on the N-terminal of gBh gene in ILTV as well.

Moreover, plaque hybridization of λGEM-12 library was again performed using as a probe an approximately 1.7 Kbp DNA fragment the farthest away from the gBh gene region of the DNA inserted into the λGEM-12/ILTV-11.5 clone. As a result, a λGEM-12/ILTV-9.6 clone was obtained into which approximately 9.6 Kbp of DNA containing an approximately 10 Kbp to 20 Kbp DNA region on the N-terminal side of gBh gene was inserted (FIG. 1). The DNA fragment inserted into this λ phage was predicted to contain UL32h gene of ILTV based on HSV-1 data.

Example 2

Subcloning of λGEM-12/ILTV-9.6 Inserted DNA

An approximately 9.6 Kbp inserted DNA fragment was digested with restriction enzymes SmaI, BamHI and EcoRI, and resulting frangments were subcloned in pUC19 plasmid in order to perform sequence analysis to confirm whether or not the λGEM-12/ILTV-9.6 inserted DNA contained UL32h gene. As a result, five plasmids were obtained containing an approximately 4 Kbp SmaI-BamHI fragment (pUCSB4), an approximately 0.5 Kbp BamHI-EcoRI fragment (pUCBE0.5), an approximately 2.5 Kbp BamHI-EcoRI fragment (pUCBE2.5), an approximately 0.6 Kbp BamHI-EcoRI fragment (pUCBE0.6) and an approximately 2.6 Kbp SmaI-BamHI fragment (pUSB2.6).

Example 3

Sequence Analysis of pUC19 Subclones of λGEM-12/ILTV-9.6

Sequence analysis using an automated DNA sequencer (ABI) was performed on the DNA inserted into the above-mentioned five subclones. Moreover, as regards pUCSB4, subclones containing smaller fragments were acquired, followed by analysis of their sequences. Next, the amino acid sequences predicted from the resulting DNA sequences were compared for homology with the UL32 amino acid sequence of HSV-1, the UL32h amino acid sequence of MDV, and the UL32h amino acid sequence of EHV.

As a result, it was found that the polypeptide encoded by the 1,749 Kbp open reading frame (ORF) (SEQ ID No. 1) contained in the pUCSB4 subclone demonstrated homology of 411 points with UL32 polypeptide of HSV-1, 454 points with UL32h polypeptide of MDV, and homology of 592 points with UL32h polypeptide of EHV according to Lipman and Pearson (Science, Vol. 227, p. 1435, 1985). In addition, this ORF encoded a polypeptide consisting of 582 amino acids. This amino acid sequence is shown in SEQ ID No. 2.

Example 4

Amiplification of UL32h Gene by PCR

UL32h gene was amplified according to the PCR method of Saiki, et al. (Science, Vol. 230, p. 1350–1354, 1985). In this PCR, pfu Taq (Stratagene) was used to alter the T5NT (actually, TTTTTTT) sequence present in UL32h gene (which has the possibility of functioning as a translation terminal signal of pox virus). Firstly, the following two fragments were prepared: a 1,487 bp DNA fragment in which restriction enzyme BamHI linker was attached to the N-terminal of UL32h gene using GGAACTGTGGATC-CGCCATGACA shown in SEQ ID No. 3 and TGCACA-CAATGGATCGCAAAAGAAGTGTTT shown in SEQ ID No. 4 as primers, and using pUCSB4 obtained in Example 2 as template; and, a 334 bp DNA fragment in which restriction enzyme SalI linker was attached to the C-terminal of UL32h gene using AACGCAATTTACAAACACT-TCTTTTGCGAT shown in SEQ ID No. 5 and CGAGAAGTCGACGTCAGACATATCGAG shown in SEQ ID No. 6 as primers, and using pUCBS4 obtained in Example 2 as template.

Next, PCR was performed using the resulting two fragments as templates, and using GGAACTGTGGATCCGC-CATGACA shown in SEQ ID No. 3 and CGAGAAGTC-GACGTCAGACATATCGAG shown in SEQ ID No. 6 as primers to obtain a 1,780 bp DNA fragment which have the modified T5NT sequence, the BamHI and SalI linkers. The resulting DNA fragment was digested with restriction enzymes BamHI and SalI and cloned into plasmid pGTPs. The inserted fragment was confirmed, and there were no variations caused during PCR whatsoever observed.

Example 5

Expression of UL32h Gene in *E. Coli* and Accuisition of Rabbit Antiserum

The DNA fragment obtained in Example 4 to which was attached restriction enzyme BamHI and SalI linkers containing UL32h gene was digested with restriction enzyme XhoI to obtain an approximately 0.75 Kb DNA fragment (UL32h/BX) and an approximately 1 Kb DNA fragment (UL32h/XS). Next, UL32h/BX was inserted into pATH11 vector digested with restriction enzymes BamHI and SalI to prepare expression vector pUL32hBX. In addition, UL32h/XS was inserted into pATH11 vector digested with restriction enzyme SalI and treated with an alkaline phosphatase to prepare an expression vector pUL32hXS. Plasmid pUL32hBX or pUL32hXS prepared in this manner was then introduced into *E. coli* strain RR-1.

Expression of plasmids pUL32hBX and pUL32hXS in *E. coli* strain RR-1 was performed in accordance with the method of Koerner, et al. (Methods in Enzymology, Vol. 194, p. 477–490, 1991), and a fusion protein with TrpE protein was recovered from the insoluble fraction of *E. coli* strain RR-1. A portion of the resulting fraction (fusion protein) was used for immunization into a rabbit in accordance with routine methods to obtain antiserum.

Separate from this, the remaining insoluble fraction was suspended in a sample buffer (Laemmli, Nature, Vol. 227, p. 680–685, 1970) and boiled. After centrifugation, the supernatant was developed with SDS-PAGE (Laemmli, Nature, Vol. 227, p. 680–685, 1970).

Figure 2:
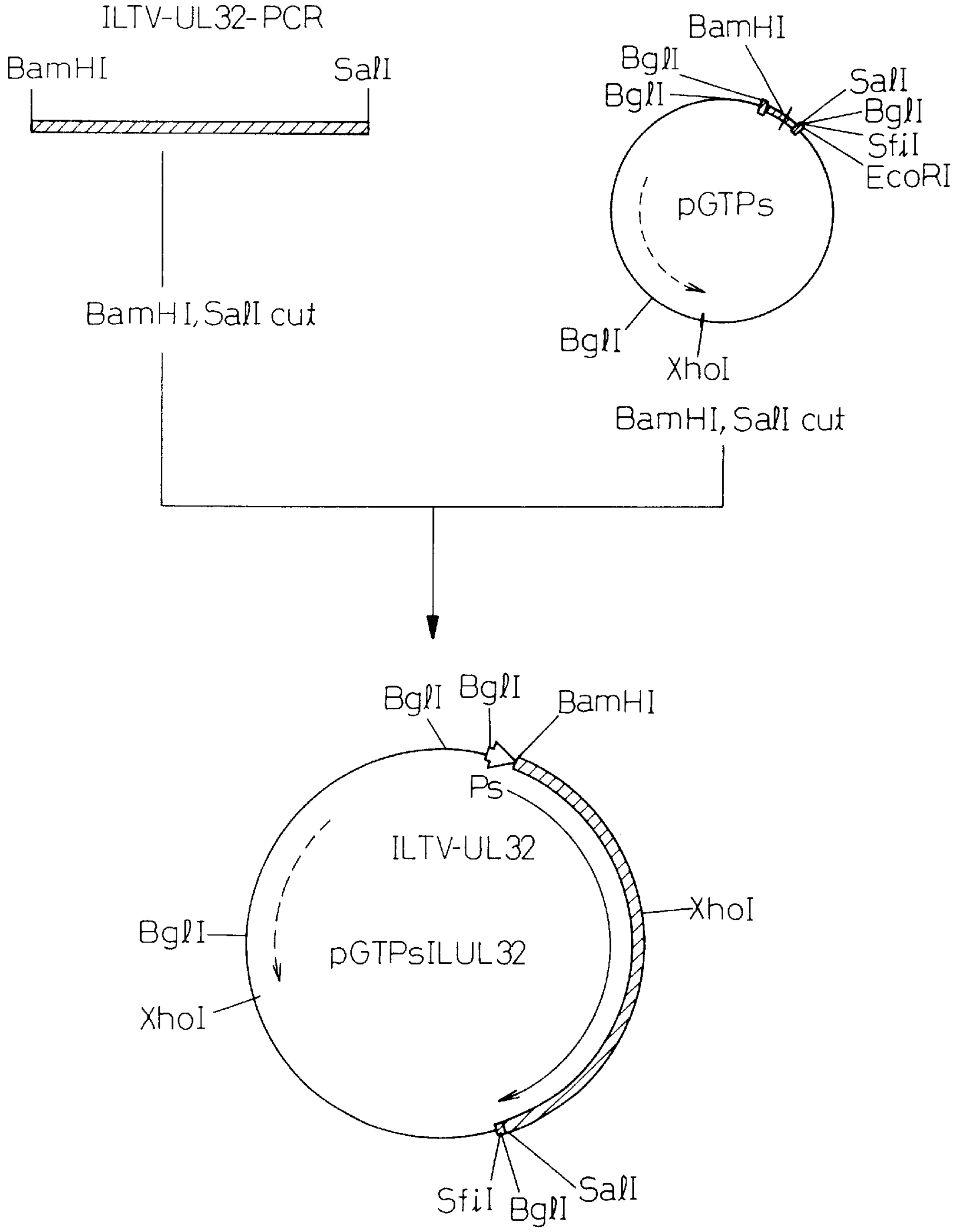
FIG. 2 is a drawing that explains the construction method of plasmid pGTPsILUL32.

As a result, as shown in FIG. 2, an approximately 65 kilodalton protein was detected from *E. coli* having pUL32hBX, and an approximately 75 kilodalton protein was detected from *E. coli* having pUL32hXS. These proteins were fusion proteins with TrpE protein, and their molecular weights obtained by subtracting the molecular weight of TrpE of approximately 37 kilodaltons corresponded to the molecular weights of the proteins predicted from each DNA sequence.

On the basis of the above, the resulting proteins were determined to respectively be portions of UL32h protein derived from NS-175 of ILTV.

Example 6

Construction of Plasmid pNP35SCV2

Genomic DNA of strain NP, a chicken pox live vaccine strain, was cleaved with restriction enzymes EcoRI or HindIII, and a resulting fragment was inserted into a long fragment resulting from similarly cleaving pUC18 with restriction enzyme EcoRI or HindlII to obtain plasmids pNP01 through pNP60. Since restriction enzyme cleaving sites ClaI, EcoRV and HpaI are not present in pUC18, pNP01 through pNP60 were cleaved with the above-mentioned restriction enzymes, and those cleaved at one location somewhere in genomic DNA cloned by any of these restriction enzymes were able to be easily selected. There were 9 types, i.e., pNP03, pNP04, pNP25, pNP26, pNP29, pNP32, pNP35, pNP36 and pNP38.

Each of these was cleaved with a restriction enzyme that was known to cleaved at one location, and only the plasmid cleaved with ClaI was blunt-ended on its ends cleaved with DNA polymerase. After treating the plasmid with an alkaline phosphatase to remove the phosphate group on the 5'-terminal, it was extracted with phenol and chloroform (1:1) and precipitated followed by recovery of the cleaved plasmid. Since lacZ gene is obtained with a promoter in the form of blunt-ended terminals from pNZ76 described in Reference Example 1 using the method described in Reference Example 2, this is ligated to the previously recovered cleaved plasmid using ligase after which *E. coli* TG1 was transformed with the resulting plasmid.

After colonies that appeared on an LB agar medium in the presence of ampicillin were cultured in an LB liquid medium in the presence of ampicillin, the plasmid was extracted using the method of Biruboim and Doly followed by selection of the plasmid into which lacZ gene was inserted. Thus, the above-mentioned 9 recombination plasmids, into which lacZ gene was inserted were obtained. These were named pNP1003, pNP1004, pNP1025, pNP1026, pNP1029, pNP1032, pNP1035, pNP1036 and pNP1038.

NP strain was infected into a single layer of CEF cells at a multiplicity of infection of 0.1, after which the cells were peeled off by treatment with trypsin 3 hr later to obtain a cell suspension. The cells were then separated by centrifugation, suspended to a concentration of $2\times10^7$ cells/ml in Saline G (0.14 M NaCl, 0.5 mM KCl, 1.1 mM $Na_2HPO_4$, 0 5 mM $MgCl_2.6H_20$, 0.011% glucose), and divided among the number of recombination plasmids prepared in Example 2. 10 $\mu$g aliquot of the recombination plasmid was added to each cell suspension, and the mixture was electroporated at room temperature using a Gene Pulser (Bio-Rad) under conditions of 3.0 KV/cm and 0.4 msec. Cells into which the plasmid were introduced were cultured for 72 hr at 37° C., after which the cells were lysed by freezing and thawing three times.

The released recombinant viruses were screened in the following manner. 10-fold serial dilutions of the solution containing progeny virus released from the lysed cells were infected into CEF cells and overlaid with 10 ml of agar medium containing growth medium. After allowing the agar to solidify at room temperature, the cells were cultured at 37° C. until typical APV plaques were formed. After about 1 week when the plaques became larger, different agar medium containing 600 μg/ml of Bluo-gal was overlaid onto each culture plate, followed by additional culturing for 24 hr at 37° C. The blue plaque was removed from the plate and the virus contained therein was recovered. Recombinant virus purification was additionally performed using the same method until all plaques formed were stained blue with Bluo-gal. This process is normally completed in 4 to 6 cycles. The recombinant viruses purified in this manner were respectively named fNP1003, fNP1004, fNP1025, fNP1026, fNP1029, fNP1032, fNP1035, fNP1036 and fNP1038.

$10^4$ PFU of recombinant AVP and NP strain as a ontrol (parent virus) were respectively inoculated by wing-web of 4 day old SPF chickens. 10 chickens were used per one experimental group. The pock size of each animal was measured on days 3, 7, 9, 11, 14, 17 and 21 after inoculation, and the mean was calculated for each group. Pock size was determined by measuring the length, width and height using a digital caliper, and calculating the volume from those three dimensions. As a result of measuring pock size, only fNP1035 exhibited pox formation similar to the parent strain, and was clearly not attenuated. Sequence analysis was performed on the recombination plasmid used to prepare recombinant fNP1035 using the non-essential region of pNP35 for the insertion site to determine its nucleotide sequence (SEQ ID No. 13). In order to insert the synthetic DNA adapter of SEQ ID No. 14 into ClaI which is a unique site of pNP35, pNP35 was cleaved with a restriction enzyme ClaI and ligated to a synthetic DNA of SEQ ID No. 14 using T4DNA ligase to transform *E. coli* TG1. Plasmid DNA was prepared from the resulting ampicillin-resistant colonies, the plasmid was selected that was cleaved with a restriction enzyme SfiI, and that plasmid was named pNP35CV. pNP35CV was cleaved with a restriction eznyme BglII and allowed to self-ligate, followed by transformation of *E. coli* TG1. The resulting ampicillin-resistant colonies were selected to prepare the plasmid. A plasmid having a length of approximately 5.7 Kbp was selected and named pNP35SCV2.

Example 7

Construction of Plasmids pGTPsILUL32 and pUC-IL-UL32 (see FIG. 2)

A fragment containing UL32h gene amplified by the same PCR method as Example 4 was digested with restriction enzymes BamHI and SalI, and a resulting fragment was introduced into the BamHI-SalI site of pGTPs which is a recombinant plasmid prepared by inserting synthetic DNA into pUC18 and obtained by the method described in Reference Example 3, so as to construct pGTPsILUL32.

Similarly, a fragment containing UL32h gene amplified by PCR was digested with restriction enzymes BamHI and salI, and a resulting fragment was inserted into the BamHI-SalI site of pUC19 so as to obtain pUC-IL-UL32.

Example 8

Figure 3:
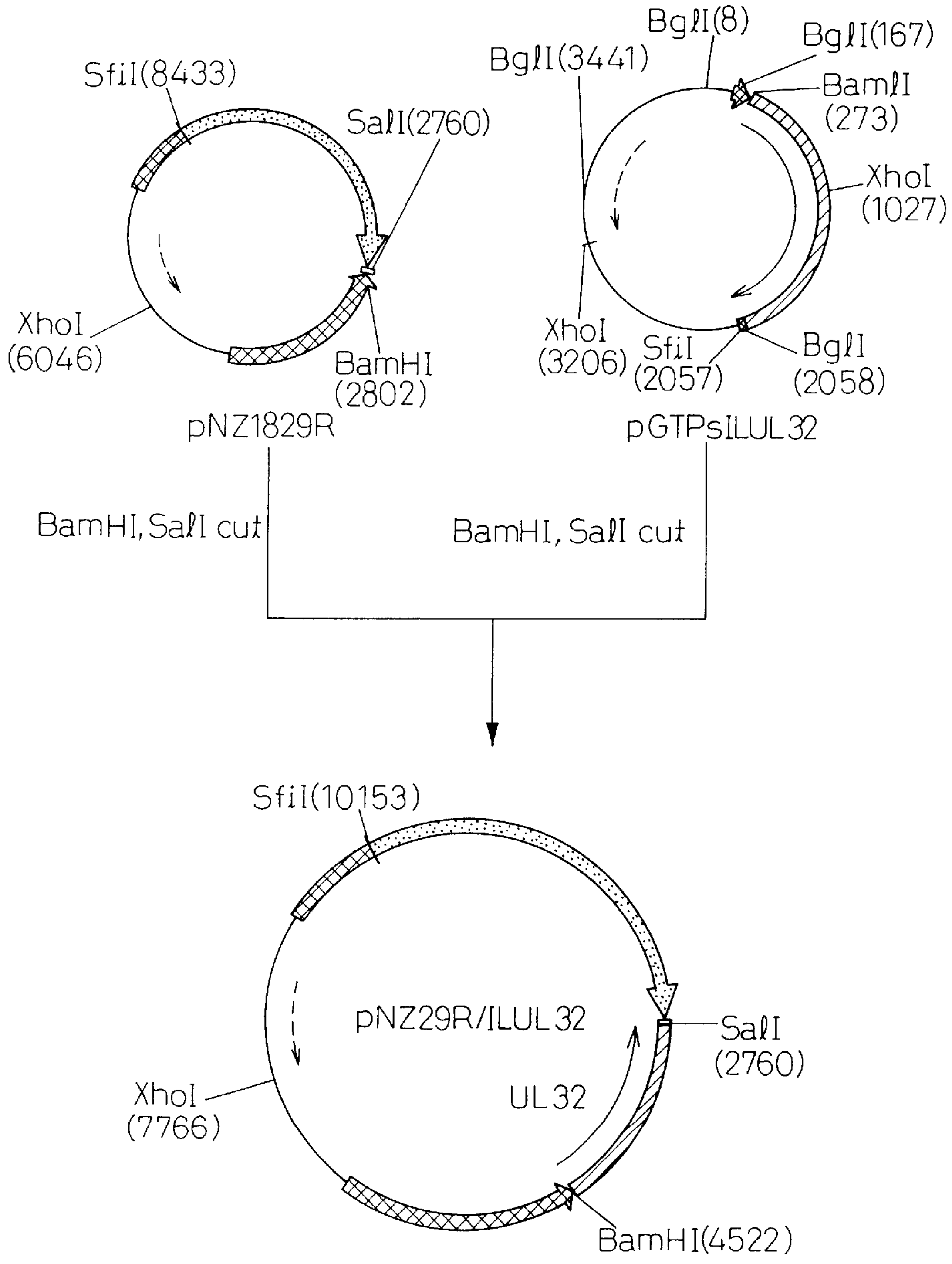
FIG. 3 is a drawing that explains the construction method of plasmid pNZ29R/ILUL32 for recombinant fowlpox virus.

Construction of Plasmid pNZ29R/ILUL32 for Recombinant Fowlpox Virus (see FIG. 3)

pUC-IL-UL32 constructed in Example 7 was digested with restriction enzymes BamHI and SalI, and introduced into the BanHI-SalI site of pNZ1829R which is a plasmid having a site that is cleaved by SfiI and constructed using the method described in Reference Example 8, to construct pNZ29R/ILUL32.

Example 9

Figure 4:
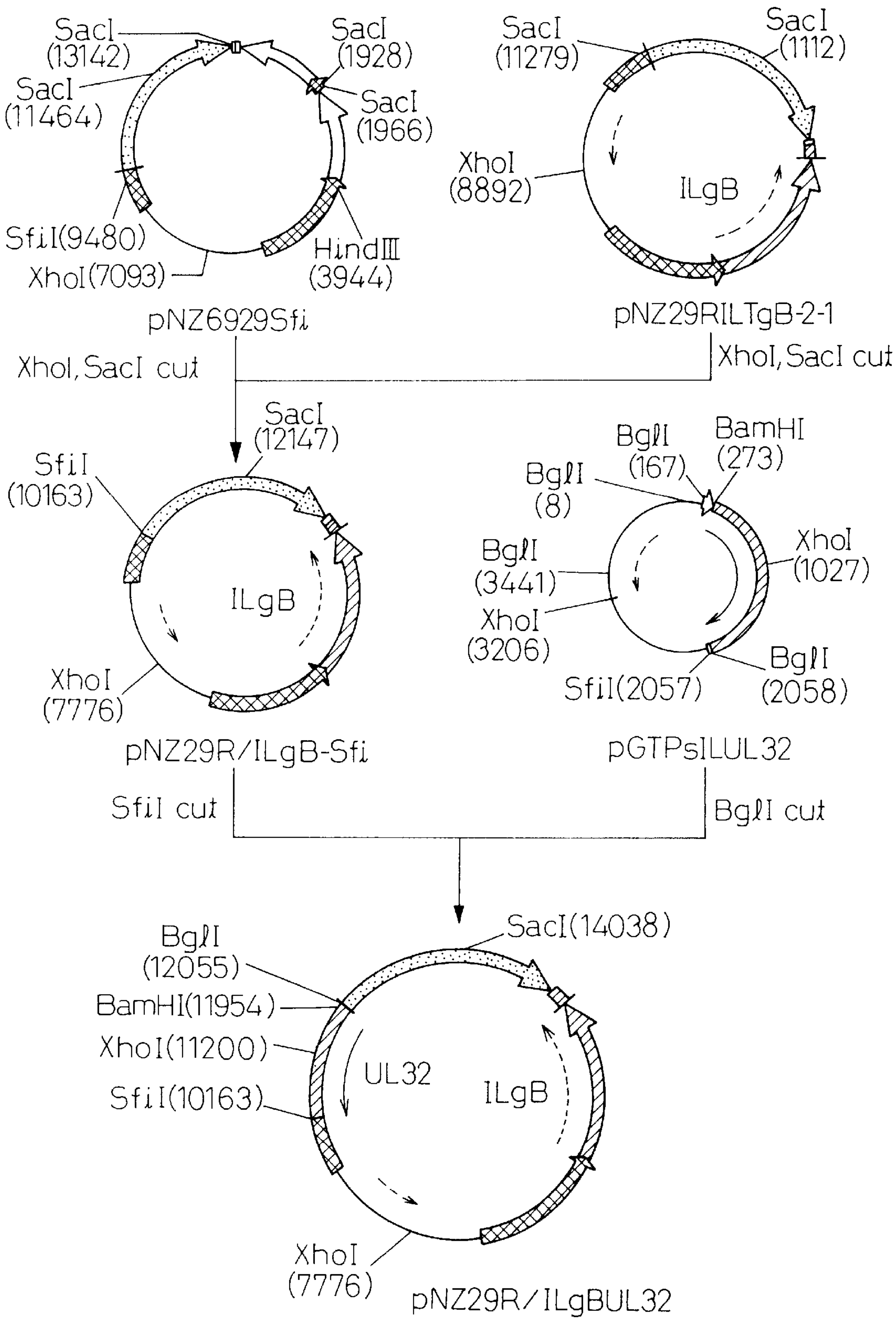
FIG. 4 is a drawing that explains the construction method of plasmid pNZ29R/ILUL32 for recombinant fowlpox virus.

Construction of Plasmid pNZ29R/ILgBUL32 for Recombinant Fowlpox Virus (see FIG. 4)

A fragment containing gB gene of ILTV obtained by cleaving with restriction enzymes XhoI and SacI a plasmid pNZ29RILTgB-2-1 constructed according to method described in Reference Example 4, was exchanged with an XhoI-SacI fragment containing the HN and F genes of NDV of pNZ6929Sfi which is a plasmid into which had been inserted antigen gene derived from the genome of Newcastle disease virus and was constructed using the method described in Reference Examples 5, 6 and 7, so as to prepare pNZ29R/ILgB-Sfi containing ILTV gB gene. This was then cleaved with restriction enzyme SfiI, and a BglI fragment containing the ILTV-UL32 gene of pGTPsILUL32 prepared in Example 9 was inserted to construct pNZ29R/ILgBUL32.

Example 10

Figure 5:
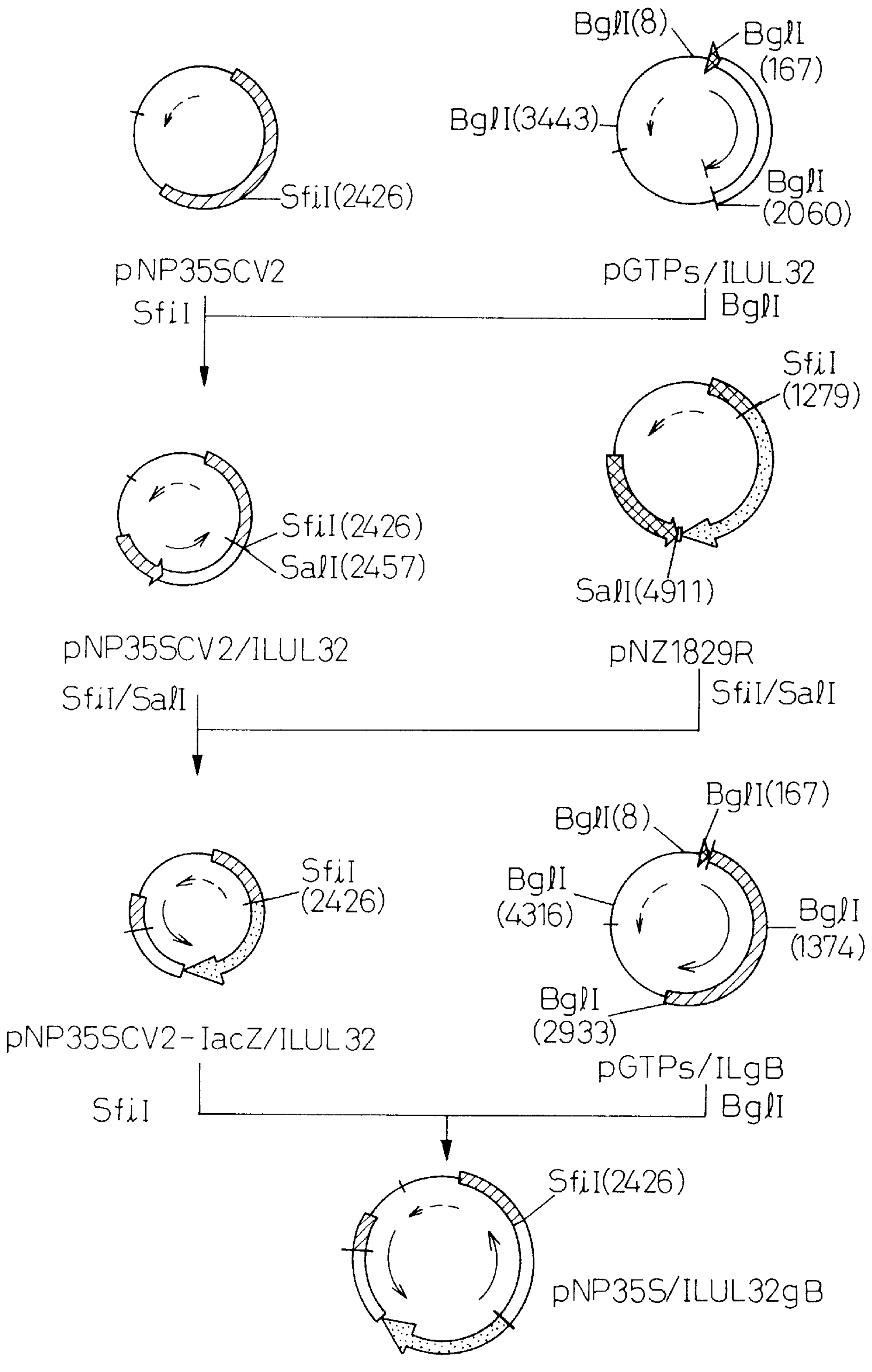
FIG. 5 is a drawing that explains the construction method of plasmid pNP35S/ILUL32gB for recombinant fowlpox virus.

Construction of Plasmid pDNP35S/ILUL32gB for Recombinant Fowlpox Virus (see FIG. 5)

pNP35SCV2 prepared in Example 6 was cleaved with a restriction enzyme SfiI, followed by insertion of a BglI fragment containing the ILTV-UL32 gene of pGTPsILU132 prepared in Example 8 to prepare pNP35SCV2/ILUL32. This was then cleaved with restriction enzymes SfiI and SalI, followed by insertion of SfiI-Sa1I fragment containing lacz of pNZ1829R described in Reference Example 8 to prepare pNZ35SCV2-lacZ/ILUL32. Separate from this, after cleaving pNZ29RILTgB-2-1 with restriction enzyme BamHI, a 2633 base fragment containing the entire length of ILTVgB gene obtained by partially digesting with restriction enzyme DraI was inserted into the BamHI-HincII site of pGTPs described in Reference Example 3 to obtain pGTPs/ILgB. A fragment containing the entire length of ILTVgB gene obtained by cleaving this pGTPs/ILgB with BglI was then inserted into the SfiI site of pNZ35SCV2-lacZ/ILUL32 to construct pNP35S/ILUL32gB.

Example 11

Preparation and Purification of Recombinant Fowlpox Virus

Pigeon pox virus NP strain or a virus having as its phenotype the formation of large plaques isolated from a fowlpox virus vaccine (Nazerian, et al., Avian Dis., Vol. 33, p. 458–465, 1989) was infected into a single layer of CEF cells at a multiplicity of infection of 0.1. Three hours later, these cells were peeled off by treatment with trypsin to form a cell suspension. This cell suspension was centrifuged to separate the cells which were then suspended to a concentration of $2\times10^7$ cells/ml in Saline G (0.14 M NaCl, 0 5 mM KCl, 1.1 mM $Na_2HPO_4$, 0.5 mM $MgCl_2.6H_20$, 0.011% glucose). 10 μg of recombination plasmid pNP35S/ILUL32gB was added to a cell suspension infected with NP strain.

On the other hand, 10 μg each of recombination plasmid pNZ29R/ILUL32 or pNZ29R/ILgBUL32 was added to a cell suspension infected with a virus having as its phenotype the formation of large plaques. This mixture was electroporated at room temperature using a Gene Pulser (Bio-Rad) under conditions of 3.0 KV/cm and 0.4 msec. The cells containing plasmid were later cultured for 72 hours at 37° C., after which the cells were lysed by freezing and thawing three times. The released recombinant viruses were screened in the manner described below.

10-fold serial dilutions of the solution containing progeny virus released from the lysed cells were infected into CE cells and overlaid with 10 ml of agar medium containing growth medium. After allowing the agar to solidify at room temperature, the cells were cultured at 37° C. until typical APV plaques were formed. After about 1 week when the plaques became larger, different agar medium containing 600 μg/ml of Bluo-gal was overlaid onto each culture plate, followed by additional culturing for 24 hr at 37° C. The blue plaque was removed from the plate and the virus contained therein was recovered. Purification of recombinant virus was additionally performed using the same method until all plaques formed were stained blue with Bluo-gal. This process is normally completed in 4 to 6 cycles.

The recombinant virus purified in this manner that was prepared from recombination plasmid pNP35S/ILUL32gB was named NP35S/ILUL32gB, that prepared from recombination plasmid pNZ29R/ILUL32 was named US29R/ILUL32, and that prepared from recombination plasmid pNZ29R/ILgBUL32 was named UL29R/ILgBUL32.

Example 12

Insertion Gene of Recombinant Fowlpox Virus and Confirmation of Expression

The three types of recombinants prepared in Example 11 were all confirmed to be located as predicted by the gB gene and UL32h gene of ILTV according to Southern hybridization. In addition, after acetone-fixing the CEF cells infected with one of these three types of recombinants, they were allowed to react with FITC-labeled anti-rabbit (goat) serum (Tago) (100-fold dilution). When observed using the indirect fluorescent antibody method, a characteristic fluorescence was observed. Moreover, anti-UL32/XS rabbit serum (100-fold dilution) obtained in Example 5 was reacted with a lysed solution of CEF cells infected with each of these three types of recombinants. After reacting with peroxidase-labeled anti-rabbit (goat) serum (Tago) (100-fold dilution), color was generated with 4-chloro-1-naphthol. As a result, a specific band was observed at the location of the predicted molecular weight of approximately 68 kd, thereby confirming that the UL32h gene of ILTV was expressed in recombinant fowlpox virus.

Example 13

Infection Defensive Effect of Chickens Inoculated with Recombinant Fowlpox Virus Against Virulent ILTV $10^4$ PFU (plaque forming units) of recombinant fowlpox virus prepared In Example 11 and recombinant fowlpox virus ILTVgB2-1 described in U.S. Pat. No. 5,443,831 were inoculated to a wing-web of SPF chickens at age 40 days. The chickens were simultaneously inoculated with ILT live vaccine (Kaketsuken) by dropping one drop into the eyes as directed (approximately 0.03 ml) ($10^{4.0}$ $TCID_{50}$/chicken or more). Eighteen days later, the chickens were challenged by inoculation of $10^{3.5}$ $EID_{50}$/0.1 ml of virulent ILTV strain NS-175 into the infraorbital sinus based on the method described in "Animal Biological Pharmaceuticals" (Animal Biological Pharmaceutical Association). The chickens were observed for clinical symptoms for 1 week after inoculation and autopsied after 1 week. Chickens that presented with clinical symptoms for 2 days or more were judged to have been infected (namely, were unable to defend against infection). Those results are shown in Table 1. In addition, with the exception of inoculating live vaccine into chickens at age 30 days instead of at age 40 days, and challenging with virulent ILTV at age 44 days instead of 18 days later (age 58 days), an experiment was conducted using an identical procedure as that described above. Those results are shown in Table 2.

TABLE 1

| | Defense rate | Defense rate |
|---|---|---|
| Uninoculated | 0/11 | (0%) |
| Live vaccine | 12/12 | (100%) |
| ILTVgB2-1 | 4/11 | (36%) |
| US29R/ILUL32 | 0/11 | (0%) |
| US29R/ILgBUL32 | 11/11 | (100%) |
| NP35S/ILUL32gB | 11/11 | (100%) |

TABLE 2

| | Defense rate | Defense rate |
|---|---|---|
| Uninoculated | 0/12 | (0%) |
| Live vaccine | 12/12 | (100%) |
| ILTVgB2-1 | 6/12 | (50%) |
| US29R/ILUL32 | 3/11 | (27%) |
| US29R/ILgBUL32 | 10/11 | (91%) |
| NP35S/ILUL32gB | 12/12 | (100%) |

According to these two tables, a certain level of defensive effect was observed in chickens inoculated with US29R/ILUL32 containing only the UL32h gene of ILTV, in comparison with chickens that were not inoculated. However, defensive effect was lower when compared with ILTVgB2-1 consisting of only the gB gene of ILTV. Surprisingly, however, in the case of the two recombinant fowlpox viruses US29R/IlgBUL32 and NP35S/ILUL32gB, in which were introduced UL32 gene in addition to gB gene, performance was verified to be equal to that of ILTV live vaccine, thereby indicating results that exceeded an additive effect of recombinant containing gB gene alone and recombinant containing UL32 gene alone (synergistic effects).

Reference Example 1

Figure 6:
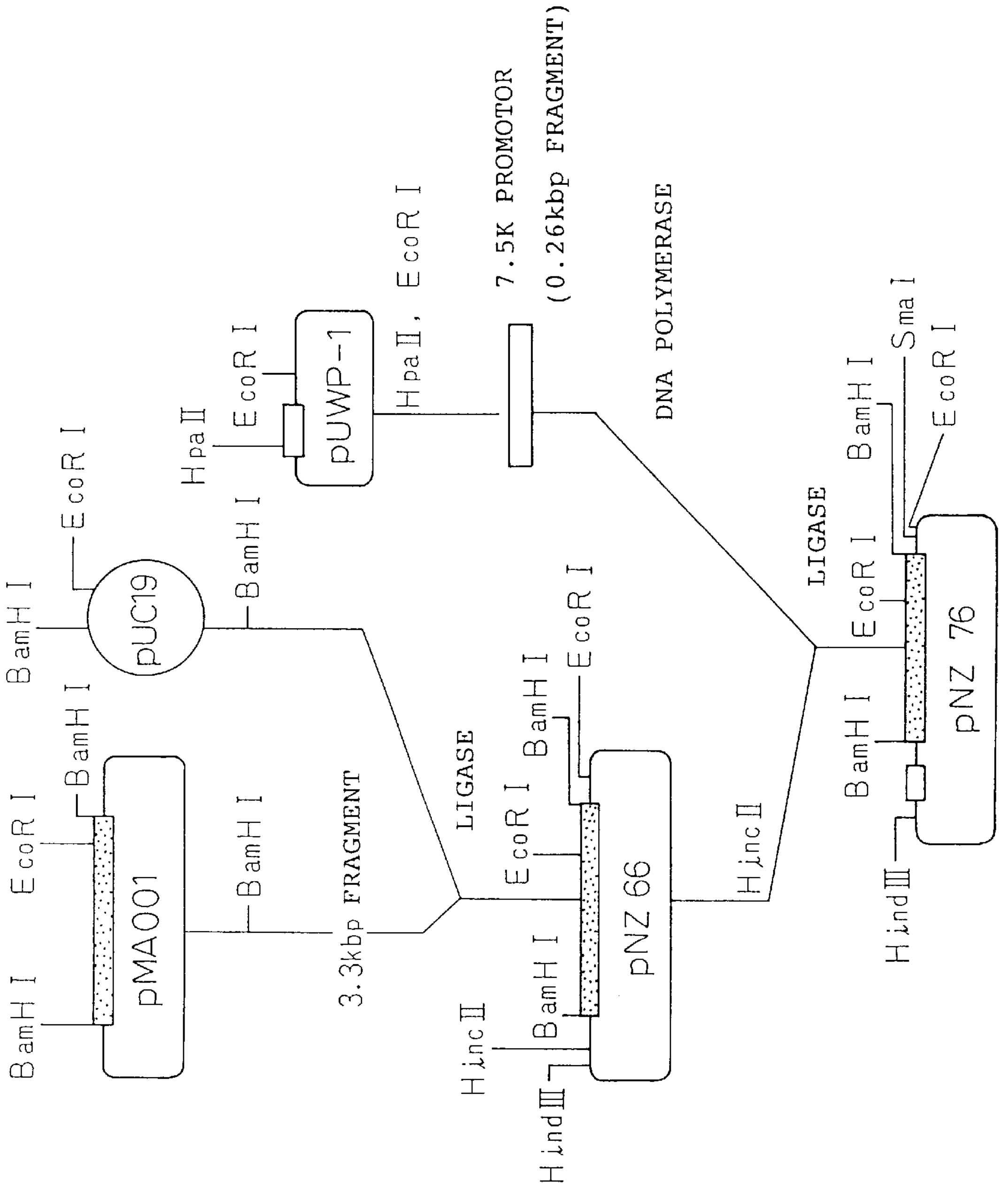
FIG. 6 is a drawing that explains the construction method of plasmid pNZ76.

Preparation of Plasmid Comprising β-Galactosidase Gene Ligated to 7.5 K Promoter (see FIG. 6)

After digesting 10 μg of pMA001 [Shirakawa, et al., Gene, 28, 127-, (1984)] with BamHI, it was extracted with phenol-chloroform (1:1) followed by ethanol precipitation to recover β-galactosidase gene (approximately 3.3 Kbp). On the other hand, after digesting 0.3 μg of pUC19 with BamHI, it was extracted with phenol-chloroform and recovered by ethanol precipitation. It was then ligated with the β-galactosidase gene prepared above to prepare hybrid plasmid pNZ66.

After digesting 40 μg of pUWP-1 with HpaII and EcoRI, an approximately 0.26 Kbp fragment containing a 7.5 K promoter was separated by 1.5% low melting point agarose gel electrophoresis (70 volts, 6 hours), followed by extraction with phenol-chloroform (1:1) and ethanol precipitation to recover the DNA. The adhesive ends of this DNA fragment were modified to blunt-ends with DNA polymerase. Next, after digesting 0.3 μg of pNZ66 with HincII, it was extracted with phenol-chloroform and recovered by ethanol precipitation, followed by ligation with the above-mentioned 0.26 Kbp 7.5 K promoter gene. The resulting hybrid plasmid was named pNZ76.

Reference Example 2

Acquisition of β-Galactosidase Gene (Blunt-ended)

After digesting 10 μg of pNZ76 with HindIII and SmaI, an approximately 3.6 Kbp fragment was separated by 0.7% low melting point agarose gel electrophoresis (40 volts, 20 hours). After confirming the DNA fragment by ethidium bromide staining, the gel was cut out and treated with phenol, followed by ethanol precipitation to recover the DNA fragment.

On the other hand, 1 μg of pNZ180 was digested with EcoRV, followed by extraction with phenol-chloroform and recovery by ethanol precipitation. 0.3 μg of the cleaved pNZ180 DNA and approximately 0.4 μg of the above-mentioned approximately 3.6 Kbp fragment (fragment comprising 7.5 K promoter DNA linked to β-galactosidase gene) were mixed, the adhesive ends were modified to blunt-ends with DNA polymerase and after extracting with phenol-chloroform, the β-galactosidase fragment was recovered by ethanol precipitation.

Reference Example 3

Figure 7:
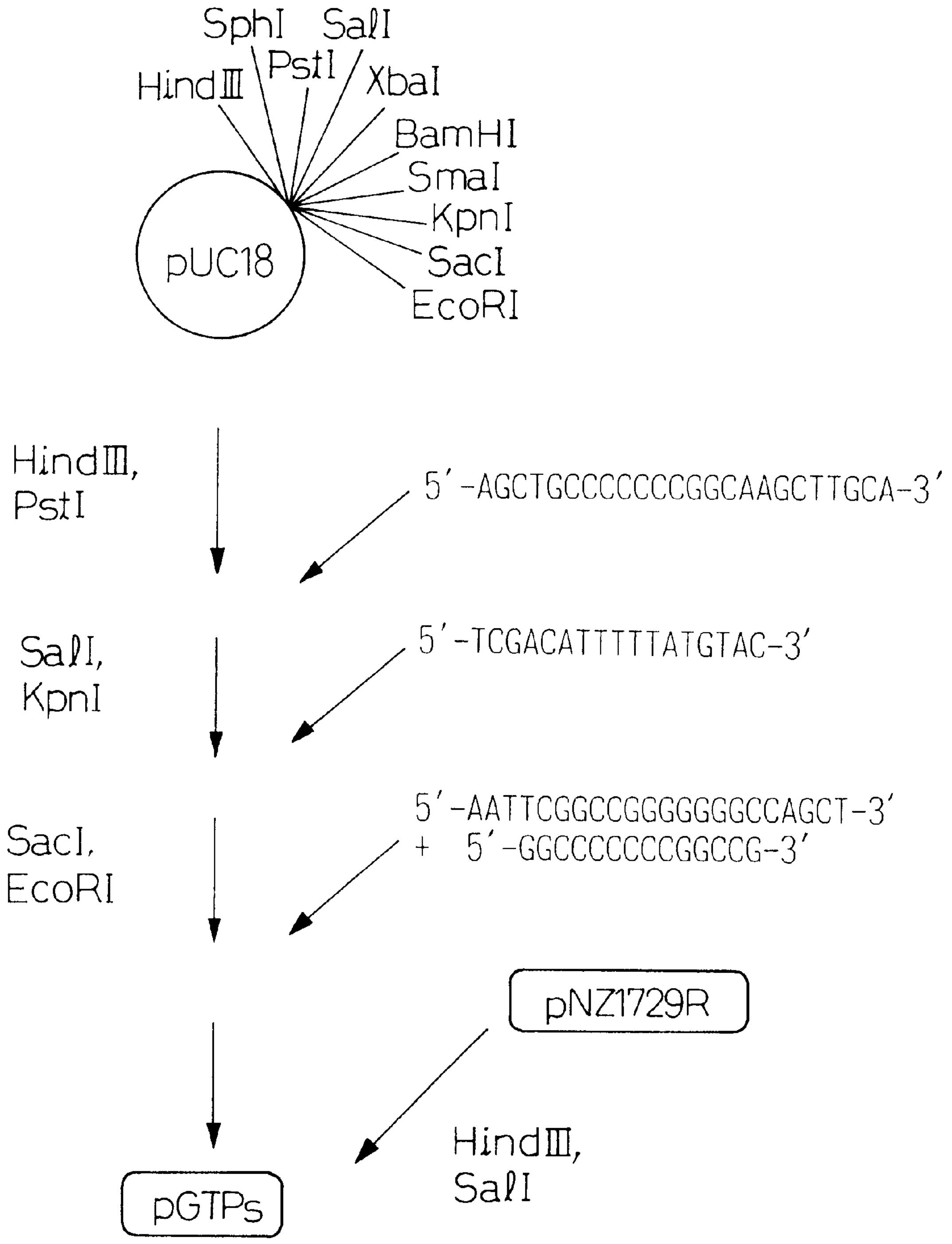
FIG. 7 is a drawing that explains the construction method of plasmid pGTPs.

Construction of Donor Plasmid pGTPs (see FIG. 7)

Synthetic DNA (5'-AGCTGCCCCCCCGCAAGCTTGCA-3' (SEQ ID No. 15)) was inserted into the HindIII-PstI site of pUC18, after which synthetic DNA (5'-TCGACATTTTATGTAC-3' (SEQ ID No. 16)) was inserted into the SalI-KpnI site of the resulting plasmid. Moreover, two annealed synthetic DNA (5'-AATTCGGCCGGGGGGGCCAGCT-31' (SEQ ID No. 17)) and (5'-GGCCCCCCCGGCCG-3' (SEQ ID No. 18)) were inserted into the SacI-EcoRI site of the resulting plasmid, and finally, plasmid pNZ1729R (Yanagida, et al., J. Virol., 66, 1402–1408, 1992) was digested with HindIII and SalI and the resulting approximately 140 bp DNA fragment was inserted into the HindIII-SacI site of this plasmid to construct plasmid pGTPs.

Reference Example 4

PCR was performed to alter the two T5NT sequences present in gB gene (which has the possibility of functioning as a translation termination signal of pox virus) in the same manner as was altered in Example 4 from the gB gene sequence of ILTV described in U.S. Pat. No. 5,443,831, and to introduce a restriction enzyme site to be inserted into a recombination plasmid.

ILTV genomic DNA was prepared using the same method as Example 1 from ILTV virulent wild strain 632 described in U.S. Pat. No. 5,443,831. PCR was performed using this DNA as a template and using as primer sets SEQ ID No. 19 and SEQ ID No. 20, SEQ ID No. 21 and SEQ ID No. 22, as well as SEQ ID No. 23 and SEQ ID No. 24 that were synthesized based on the sequence data described in U.S. Pat. No. 5,443,831 to prepare three fragments in which was introduced a restriction enzyme site (BamHI and XhoI) to alter the two T5NT sequences and insert a recombination plasmid. An altered ILTV gB gene was then prepared by performing PCR using these three fragments as templates and the primers of SEQ ID No. 15 and SEQ ID No. 20. A resulting fragment was digested with BamHI and XhoII and inserted into the BamHI-SalI site of plasmid pNZ172R (Yanagida, et al., J. Virol., 66, 1402–1408, 1992) to construct a recombination plasmid pNZ29RILTgB-2-1. Furthermore, recombinant fowlpox virus prepared using this recombination plasmid pNZ29RILTgB-2-1 is the recombinant fowlpox virus described in U.S. Pat. No. 5,443,831.

Reference Example 5

Figure 8:
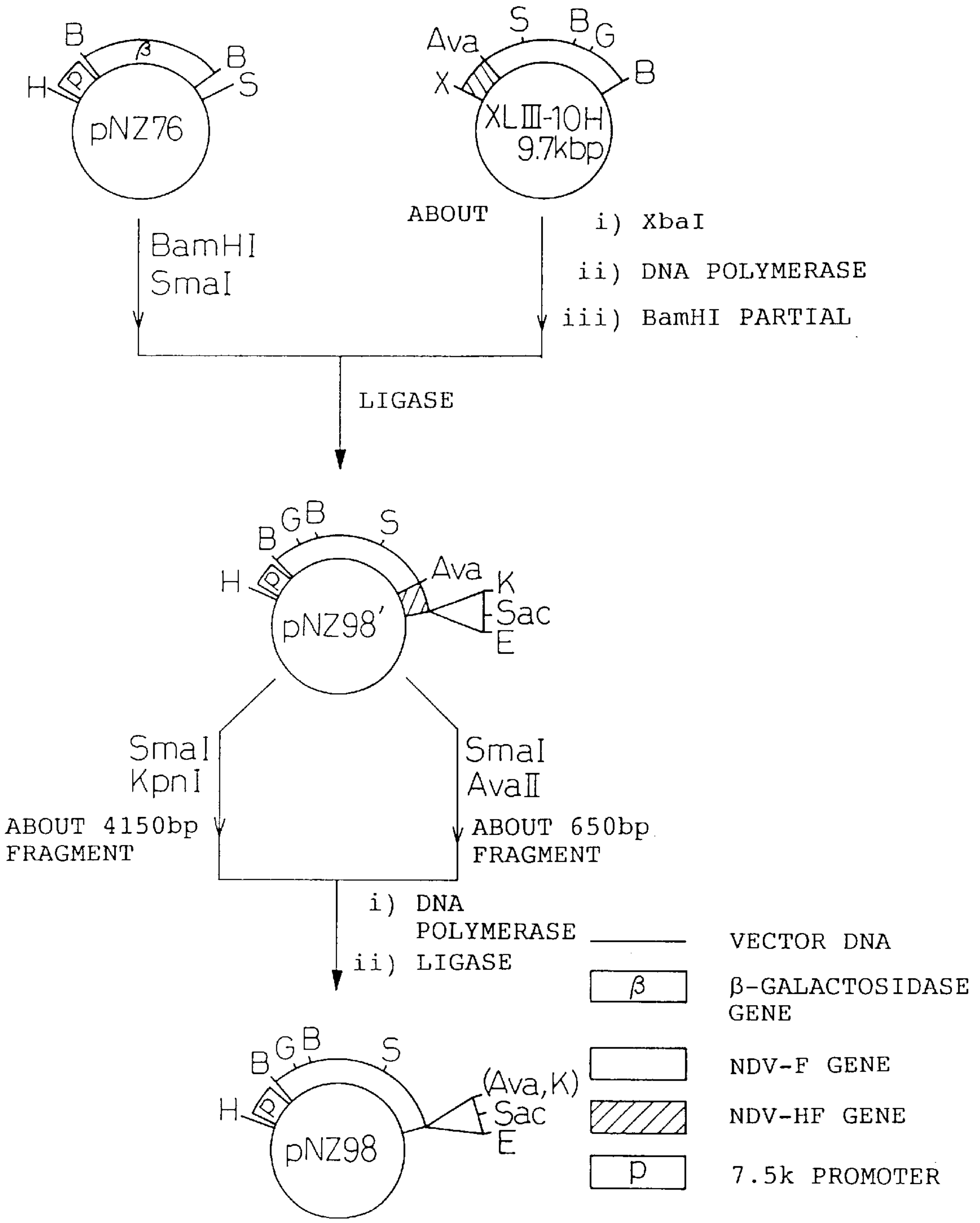
FIG. 8 is a drawing that explains the construction method of plasmid pNZ98.

Preparation of Hybrid Plasmid (pNZ98) Comprising Promoter Linked with F Gene DNA under its Control (see FIG. 8)

Plasmid XLIII-10H containing cDNA of the F and HN genes of NDV [Virus Research, 7, 241–255 (1987)] was acquired from Associate Professor Masao Kawakida of the Department of Education, Tokyo University.

After digesting 4 μg of this plasmid XLIII-10H with XbaI, the adhesive ends was modified to blunt-ends with DNA polymerase, followed by extraction with phenol-chloroform and recovery by ethanol precipitation. After partially digesting the recovered DNA with BamHI, it was applied to 0.8% agarose gel electrophoresis to recover a fragment containing the entire approximately 2.1 Kbp F gene. On the other hand, hybrid plasmid (pNZ76), comprising the promoter prepared in (3) of Reference Example 1 linked to a DNA under its control that encodes an easily detectable enzyme, was digested with BamHI and SamI to recover an approximately 3.0 Kbp BamHI-SmaI fragment from which the lacZ gene portion had been eliminated. This approximately 3.0 Kbp fragment and the above-mentioned approximately 2.1 Kbp fragment were ligated with ligase, followed by transformation of competent *E. coli* strain TG1. Plasmid was prepared from colonies growing on LB agar medium containing 50 μg/ml of ampicillin, the target clone was confirmed by cleaving with restriction enzyme, and that plasmid was named pNZ98'. Plasmid pNZ98' contained not only the entire length of the F gene, but also approximately 300 bp of the 5' terminal of HN gene. In order to remove this portion, pNZ98' was digested with SmaI and KpnI, and an approximately 4150 bp SmaI-KpnI fragment was recovered by 0.8% agarose gel electrophoresis. In addition, pNZ98' was also digested with SmaI and AvaII, and an approximately 650 bp SmaI-AvaII fragment was recovered by 1.5% agarose gel electrophoresis. These two fragments were mixed, and after modification from the adhesive ends to blunt ends by DNA polymerase, they were ligated by ligase, followed by transformation of competent *E. coli* strain TG1. Plasmid was prepared from colonies growing on LB agar medium containing 50 μg/ml of ampicillin, the plasmid that was again able to be cleaved with restriction enzyme SmaI was selected, and that plasmid was named pNZ98.

Reference Example 6

Preparation of Hybrid Plasmid pNZ87 Comprising Promoter and Linked HN Gene DNA of NDV under its from Hybrid Phage mp10- HN180 Control pNZ76 was digested with BamHI and an approximately 2.9 Kbp fragment not containing β-galactosidase gene was recovered by 0.8% agarose gel electrophoresis. On the other hand, after digesting hybrid phage mp10-HN180 with BglII and BamHI, an approximately 1.8 Kbp HN gene DNA fragment was recovered by 0.8% agarose gel electrophoresis. Both were ligated with ligase, competent *E. coli* strain TG-1 was transformed with the resulting plasmid, the plasmid was extracted in accordance with conventional methods, and the hybrid plasmid containing HN gene was detected. This hybrid plasmid was named pNZ87.

Reference Example 7

Figure 9:
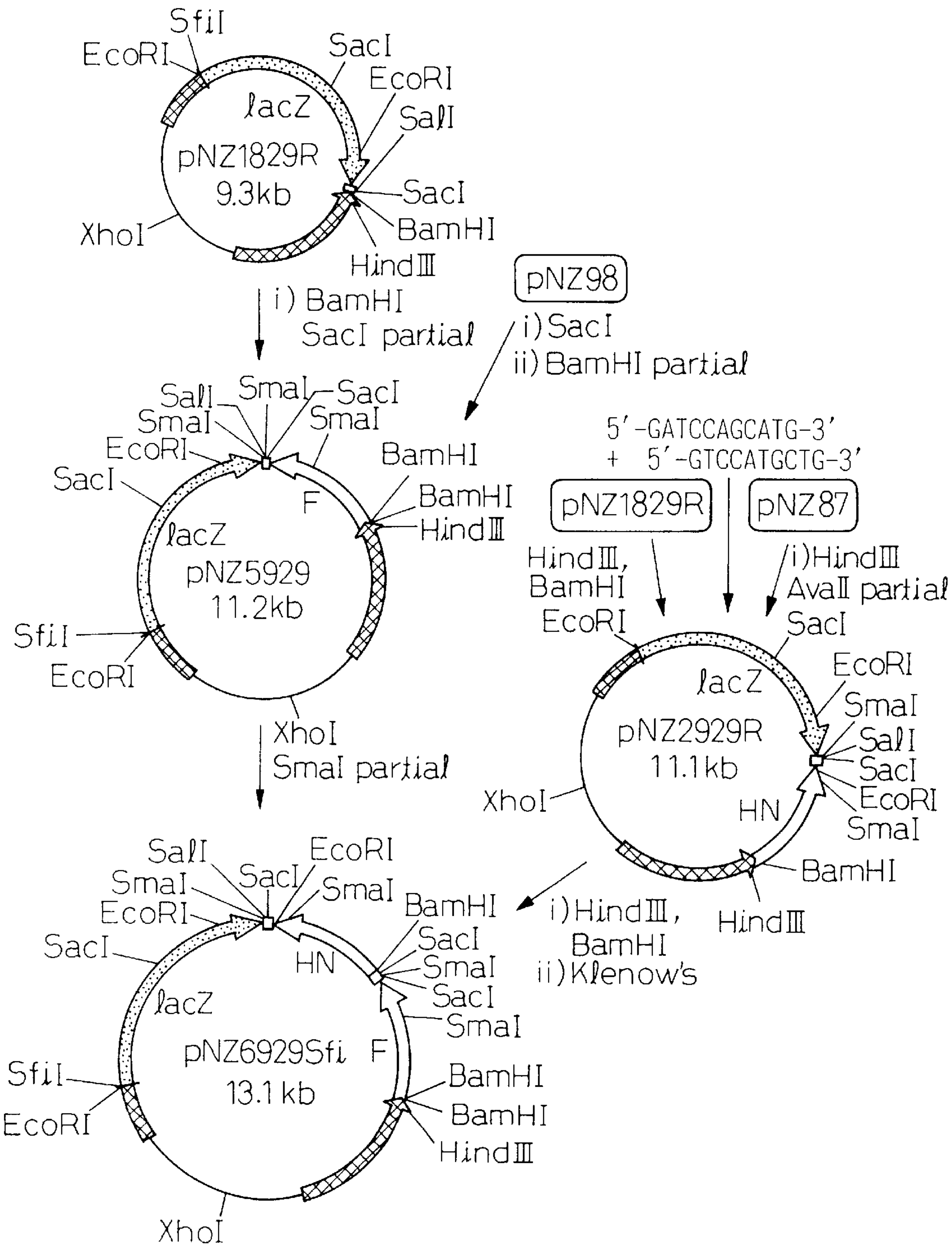
FIG. 9 is a drawing that explains the construction method of plasmid pNZ6929Sfi.

Construction of Acceptor Plasmid pNZ6929Sfi (see FIG. 9)

After partially digesting plasmid pNZ98 (plasmid having F antigen gene originating in Newcastle disease virus described in Reference Example 5) with SacI, it was additionally partially digested with BamHI to recover an approximately 1.9 Kbp DNA fragment. On the other hand, after digesting plasmid pNZ1829R with BamHI, it was additionally partially digested with SacI, followed by insertion of the above-mentioned 1.9 Kbp BamHI-SacI DNA fragment to construct the target plasmid pNZ5929.

The annealed product of two synthetic DNAs described in SEQ ID No. 25 and SEQ ID No. 26 (5'-GATCCAGCATG-3' (SEQ ID No. 25) and 5'-GTCCATGCTG-3' (SEQ ID No. 26)) was added to the large fragment obtained by cleaving plasmid pNZ87 (plasmid having HN antigen gene originating in Newcastle disease virus described in Reference Example 6) with HindIII, and the 95 bp fragment obtained by digesting plasmid pNZ1829R with HindIII and BamHI to construct plasmid pNZ2929R. After cleaving this plasmid pNZ2929R with HindIII, it was partially digested with BamHI to obtain an approximately 1.9 Kbp fragment. After blunt-ending the ends of this fragment using a Krenow fragment of DNA polymerase, it was inserted into plasmid pNZ5929 digested with SmaI to obtain acceptor plasmid pNZ6929Sfi.

Reference Example 8

Figure 10:
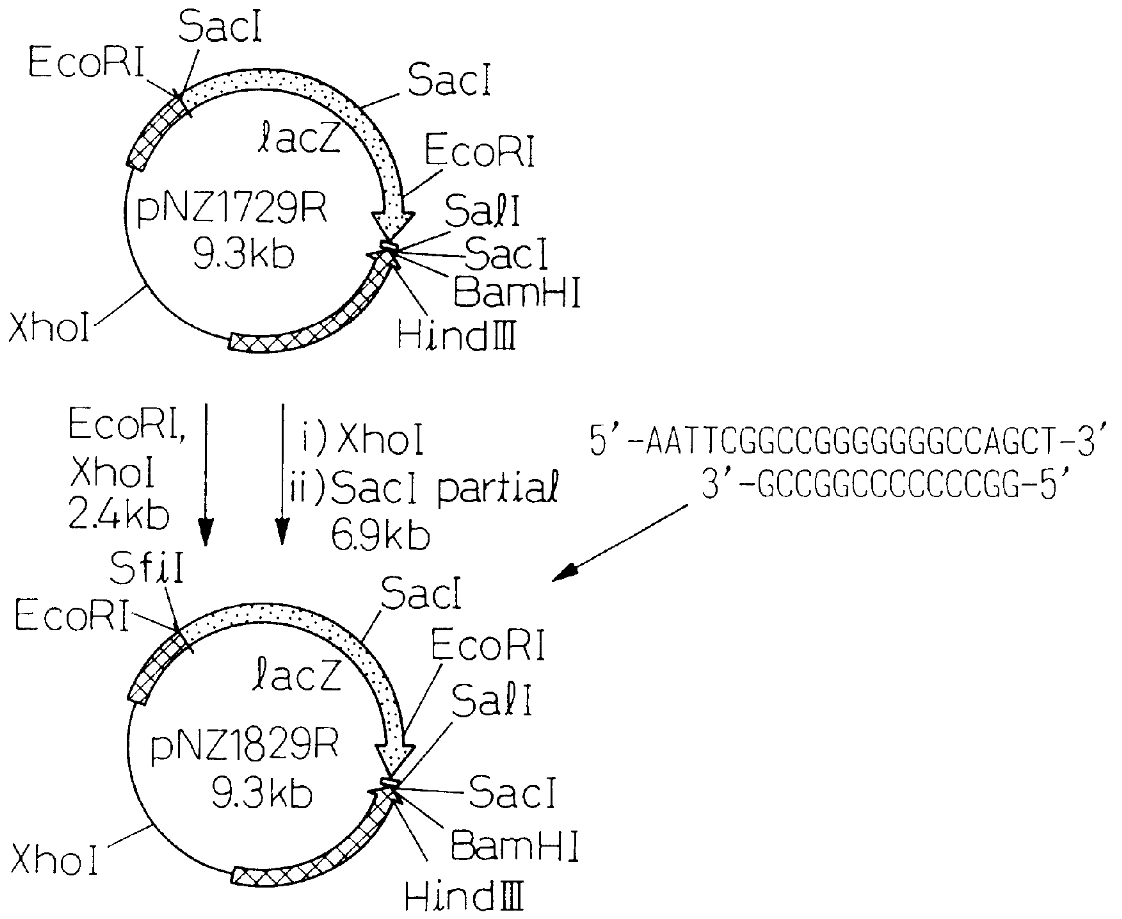
FIG. 10 is a drawing that explains the construction method of plasmid pNZ1829R.

Construction of Acceptor Plasmid pNZ1829R (see FIG. 10)

Plasmid pNZ1729R (Yanagida, et al., J. Virol., 66, 1402–1408, 1992) was digested with EcoRI and SacI, and a synthetic adapter containing an SfiI site, at which two synthetic DNAs described in SEQ ID No. 27 and SEQ ID No. 28 (5'-AATTCGGCCGGGGGGGCCAGCT-3' (SEQ ID No 27) and 5'-GGCCCCCCCGGCCG-3' (SEQ ID No. 28)) were annealed, was inserted at this site to construct plasmid pNZ1829R.

What is claimed is:

1. An isolated DNA molecule that encodes a polypeptide that has the amino acid sequence described in SEQ ID No. 2 or an amino acid sequence that is at least 80% homologous with said amino acid sequence, wherein the DNA encoding the amino acid sequence that is at least 80% homologous with said amino acid sequence hybridizes with a nucleic acid having the nucleotide sequence described in SEQ ID No. 1 under conditions of 42° C., 2% skim milk, 6-fold concentrated SSC (6×SSC; pH 7.0) and 0.1% SDS, and which protein induces an immune response against infectious laryngotracheitis virus.

2. A recombinant DNA molecule containing the DNA as set forth in claim 1 and at least one additional DNA sequence.

3. A recombinant vector that contains a DNA sequence of a DNA molecule as set forth in claim 1.

4. A transformant having a DNA molecule as set forth in claim 1.

5. A recombinant virus having a DNA molecule as set forth in claim 1.

6. A live vaccine for infectious laryngotracheitis virus comprising as its active ingredient a recombinant virus as set forth in claim 5.

7. A recombinant virus as set forth in claim 5 wherein said virus is a virus that infects fowls.

8. A live vaccine for infectious laryngotracheitis virus comprising as its active ingredient a recombinant virus as set forth in claim 7.

9. A method for immunizing fowls comprising administering a live vaccine as set forth in claim 8.

10. A recombinant virus as set forth in claim 5 wherein said virus is an avipox virus.

11. A live vaccine for infectious laryngotracheitis virus comprising as its active ingredient a recombinant virus as set forth in claim 10.

12. A method for immunizing fowls comprising administering a live vaccine as set forth in claim 11.

13. A recombinant virus as set forth in claim 5 wherein said virus is a fowlpox virus.

14. A live vaccine for infectious laryngotracheitis virus comprising as its active ingredient a recombinant virus as set forth in claim 13.

15. A method for immunizing fowls comprising administering a live vaccine as set forth in claim 14.

16. An isolated polypeptide having the amino acid sequence described in SEQ ID No. 2 or an amino acid sequence that is at least 80% homologous with said amino acid sequence, wherein the amino acid sequence that is at least 80% homologous with said amino acid sequence is encoded by a DNA that hybridizes with a nucleic acid having the nucleotide sequence described in SEQ ID No. 1 under conditions of 42° C., 2% skim milk, 6-fold concentrated SSC (6×SSC; pH 7.0) and 0.1% SDS, and induces an immune response against infectious laryngotracheitis virus.

17. An immunogenic composition comprising as its active ingredient a polypeptide described in claim 8 or its pharmaceutically acceptable salt.

18. An isolated DNA molecule that encodes a polypeptide that has the amino acid sequence described in SEQ ID No. 2.

19. A recombinant DNA molecule containing the DNA as set forth in claim 18 and at least one additional DNA sequence.

20. A recombinant vector that contains a DNA sequence of a DNA molecule as set forth in claim 18.

21. A transformed host cell having a DNA molecule as set forth in claim 18.

22. A recombinant virus having a DNA molecule as set forth in claim 18.

23. A live vaccine for infectious laryngotracheitis virus comprising as its active ingredient a recombinant virus as set forth in claim 22.

24. A recombinant virus as set forth in claim 18 wherein said virus is a virus that infects fowls.

25. A live vaccine for infectious laryngotracheitis virus comprising as its active ingredient a recombinant virus as set forth in claim 24.

26. A method for immunizing fowls comprising administering a live vaccine as set forth in claim 25.

27. A live vaccine for infectious laryngotracheitis virus comprising as its active ingredient a recombinant virus as set forth in claim 29.

28. A method for immunizing fowls comprising administering a live vaccine as set forth in claim 27.

29. A recombinant virus as set forth in claim 22 wherein said virus is an avipox virus.

30. A live vaccine for infectious laryngotracheitis virus comprising as its active ingredient a recombinant virus as set forth in claim 29.

31. A method for immunizing fowls comprising administering a live vaccine as set forth in claim 30.

32. A recombinant virus as set forth in claim 22 wherein said virus is a fowlpox virus.

33. A polypeptide having the amino acid sequence described in SEQ ID No. 2.

34. An immunogenic composition comprising as its active ingredient a polypeptide described in claim 33 or its pharmacologically acceptable salt.

* * * * *

SEQUENCE LISTING

<160> NUMBER OF SEQ ID NOS: 28

<210> SEQ ID NO 1
<211> LENGTH: 1749
<212> TYPE: DNA
<213> ORGANISM: Infectious laryngotracheitis virus
<220> FEATURE:
<223> OTHER INFORMATION: Nucleotide sequence of UL 32 gene of infectious laryngotracheitis virus
<400> SEQUENCE: 1
atgacatcca aacgatcaac tgcagaaact cgcactgaac tttccaaggg atggaaagct 60
ggagtgctct caaaactata tactggctac gacccggcga ttctgacgtt taatgacaag 120
ttgtcggacg aactattgta tggagctcac ctaattgaaa tatatcatga agaaagtaca 180
gaacaagctg aagaacaaaa cagaattccg gacattgatt ctttcgtaga aaccatggct 240
gacttataca ccctagataa atcatgcgcc gtctgcaaga ttattaccaa atatcaaaaa 300
aaattccccg tgactcccga atggatggtg gactactctt tattgtgctt caaatctcaa 360
agcatccccc tgtgtgctac atctaccttc ataactgctt ttgagttcat cttcatcatg 420
gacaaacact acttgcattc ccacagcacc tctttagttg gcgctataag ccgtcgggaa 480
ttttccctcg gggatattca gaagcacttc ttttttaacg gctgtttcaa agcggtggaa 540
gggggactgg actctaaaat agatctaaat aattattcgt tcctagtgca gtcggtagca 600
cgctatgcgt tactatctac tagatattca agagcactta gggcaaaaat tgccccggtc 660
tctggcgcgt ctgcagattt caacttccaa aaaagtagcg gaatggccgt ggctttgtta 720
aaatggcgtg agtatgccag accactcgag tgtttttgct ccgcgcagtg tatgttaaag 780
aggaaaaata cagagaatgc ctccttcgct tttcgaacct gtgcgcaaaa agctgcttta 840
gaagatatta ccccggattc aaaatatgtg gaaggggggac caagcgaaac cctgacaacc 900
ccaagtaaat ggggatttac cgacctgacg gcattattaa ttgctggaac agccggtatg 960

-continued

```
ccaaatcggg aactcgatgc cagctgcagc gacgagcctg agtatgatga tacaaatgat   1020

aatggagaaa atttcgttgc ccctataatt cggacaagaa ataccgtagt ggagaacttt   1080

cacgcaacgc taatccaaca ggtcaaaaat actaggctcc ccaagacagc gaagcagtac   1140

atttgcgaca ataccaaacc atcacttgcc attggcccaa ttttggcgtc tattttgcct   1200

cacccgacta gccgaggaga tactggaggg gaatgcgtgt tgtgcaatct catgcttact   1260

cgggaacact ggcatgctct tcgaaagctg aaaagtaaag tagtcggctg cagtaacgta   1320

aatagcagct tgttcgatgg gattgaacca gcattagaaa cgttcgaaga ctatactgcg   1380

ttaaacgatg gggggcgaat gttaacctta ttgaggatgg ccggggcaaa cgcaatttac   1440

aaacactttt tttgcgatcc attgtgtgca gttaatacgc ttcgcgtaaa tccaaaagtt   1500

ttgtgggaag gccaacccaa ggacccagaa ctgctgcagc tttataaagc cgaaatcgcc   1560

acggctaaca tatttcaaga acgggtttgc cgcgggctgt ggattctagc cttcacattt   1620

aaagcttacc agctttctcc tcctcgccct accgctttaa attctttcat tcgcggcgct   1680

gagacctatt tagagaggca cggaatcagc tgcattgctt tggaacacgc actgactcga   1740

tatgtctga                                                           1749
```

<210> SEQ ID NO 2
<211> LENGTH: 582
<212> TYPE: PRT
<213> ORGANISM: Infectious laryngotracheitis virus
<220> FEATURE:
<223> OTHER INFORMATION: Amino acid sequence of L32h polypeptide of infectious laryngotracheitis virus

<400> SEQUENCE: 2

```
Met Thr Ser Lys Arg Ser Thr Ala Glu Thr Arg Thr Glu Leu Ser Lys
1               5                   10                  15

Gly Trp Lys Ala Gly Val Leu Ser Lys Leu Tyr Thr Gly Tyr Asp Pro
            20                  25                  30

Ala Ile Leu Thr Phe Asn Asp Lys Leu Ser Asp Glu Leu Leu Tyr Gly
        35                  40                  45

Ala His Leu Ile Glu Ile Tyr His Glu Glu Ser Thr Glu Gln Ala Glu
    50                  55                  60

Glu Gln Asn Arg Ile Pro Asp Ile Asp Ser Phe Val Glu Thr Met Ala
65                  70                  75                  80

Asp Leu Tyr Thr Leu Asp Lys Ser Cys Ala Val Cys Lys Ile Ile Thr
                85                  90                  95

Lys Tyr Gln Lys Lys Phe Pro Val Thr Pro Glu Trp Met Val Asp Tyr
            100                 105                 110

Ser Leu Leu Cys Phe Lys Ser Gln Ser Ile Pro Leu Cys Ala Thr Ser
        115                 120                 125

Thr Phe Ile Thr Ala Phe Glu Phe Ile Phe Ile Met Asp Lys His Tyr
    130                 135                 140

Leu His Ser His Ser Thr Ser Leu Val Gly Ala Ile Ser Arg Arg Glu
145                 150                 155                 160

Phe Ser Leu Gly Asp Ile Gln Lys His Phe Phe Phe Asn Gly Cys Phe
                165                 170                 175

Lys Ala Val Glu Gly Gly Leu Asp Ser Lys Ile Asp Leu Asn Asn Tyr
            180                 185                 190

Ser Phe Leu Val Gln Ser Val Ala Arg Tyr Ala Leu Leu Ser Thr Arg
        195                 200                 205
```

-continued

```
Tyr Ser Arg Ala Leu Arg Ala Lys Ile Ala Pro Val Ser Gly Ala Ser
    210                 215                 220

Ala Asp Phe Asn Phe Gln Lys Ser Ser Gly Met Ala Val Ala Leu Leu
225                 230                 235                 240

Lys Trp Arg Glu Tyr Ala Arg Pro Leu Glu Cys Phe Cys Ser Ala Gln
                245                 250                 255

Cys Met Leu Lys Arg Lys Asn Thr Glu Asn Ala Ser Phe Ala Phe Arg
            260                 265                 270

Thr Cys Ala Gln Lys Ala Ala Leu Glu Asp Ile Thr Pro Asp Ser Lys
        275                 280                 285

Tyr Val Glu Gly Gly Pro Ser Glu Thr Leu Thr Thr Pro Ser Lys Trp
    290                 295                 300

Gly Phe Thr Asp Leu Thr Ala Leu Leu Ile Ala Gly Thr Ala Gly Met
305                 310                 315                 320

Pro Asn Arg Glu Leu Asp Ala Ser Cys Ser Asp Glu Pro Glu Tyr Asp
                325                 330                 335

Asp Thr Asn Asp Asn Gly Glu Asn Phe Val Ala Pro Ile Ile Arg Thr
            340                 345                 350

Arg Asn Thr Val Val Glu Asn Phe His Ala Thr Leu Ile Gln Gln Val
        355                 360                 365

Lys Asn Thr Arg Leu Pro Lys Thr Ala Lys Gln Tyr Ile Cys Asp Asn
    370                 375                 380

Thr Lys Pro Ser Leu Ala Ile Gly Pro Ile Leu Ala Ser Ile Leu Pro
385                 390                 395                 400

His Pro Thr Ser Arg Gly Asp Thr Gly Gly Glu Cys Val Leu Cys Asn
                405                 410                 415

Leu Met Leu Thr Arg Glu His Trp His Ala Leu Arg Lys Leu Lys Ser
            420                 425                 430

Lys Val Val Gly Cys Ser Asn Val Asn Ser Ser Leu Phe Asp Gly Ile
        435                 440                 445

Glu Pro Ala Leu Glu Thr Phe Glu Asp Tyr Thr Ala Leu Asn Asp Gly
    450                 455                 460

Gly Arg Met Leu Thr Leu Leu Arg Met Ala Gly Ala Asn Ala Ile Tyr
465                 470                 475                 480

Lys His Phe Phe Cys Asp Pro Leu Cys Ala Val Asn Thr Leu Arg Val
                485                 490                 495

Asn Pro Lys Val Leu Trp Glu Gly Gln Pro Lys Asp Pro Glu Leu Leu
            500                 505                 510

Gln Leu Tyr Lys Ala Glu Ile Ala Thr Ala Asn Ile Phe Gln Glu Arg
        515                 520                 525

Val Cys Arg Gly Leu Trp Ile Leu Ala Phe Thr Phe Lys Ala Tyr Gln
    530                 535                 540

Leu Ser Pro Pro Arg Pro Thr Ala Leu Asn Ser Phe Ile Arg Gly Ala
545                 550                 555                 560

Glu Thr Tyr Leu Glu Arg His Gly Ile Ser Cys Ile Ala Leu Glu His
                565                 570                 575

Ala Leu Thr Arg Tyr Val
            580
```

<210> SEQ ID NO 3
<211> LENGTH: 23
<212> TYPE: DNA
<213> ORGANISM: Artificial Sequence
<220> FEATURE:
<223> OTHER INFORMATION: Primer -continued

<400> SEQUENCE: 3
ggaactgtgg atccgccatg aca 23

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
tgcacacaat ggatcgcaa aagaagtgttt 30

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
aacgcaattt acaaacactt cttttgcgat 30

<210> SEQ ID NO 6
<211> LENGTH: 27
<212> TYPE: DNA
<213> ORGANISM: Artificial Sequence
<220> FEATURE:
<223> OTHER INFORMATION: Primer

<400> SEQUENCE: 6
cgagaagtcg acgtcagaca tatcgag 27

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
agctgccccc ccggcaagct tgca 24

<210> SEQ ID NO 8
<211> LENGTH: 17
<212> TYPE: DNA
<213> ORGANISM: Artificial Sequence
<220> FEATURE:
<223> OTHER INFORMATION: Primer

<400> SEQUENCE: 8
tcgacatttt tatgtac 17

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
aattcggccg ggggggccag ct 22

<210> SEQ ID NO 10

-continued

<211> LENGTH: 14
<212> TYPE: DNA
<213> ORGANISM: Artificial Sequence
<220> FEATURE:
<223> OTHER INFORMATION: Primer

<400> SEQUENCE: 10
ggcccccccg gccg 14

<210> SEQ ID NO 11
<211> LENGTH: 11
<212> TYPE: DNA
<213> ORGANISM: Artificial Sequence
<220> FEATURE:
<223> OTHER INFORMATION: Primer

<400> SEQUENCE: 11
gatccagcat g 11

<210> SEQ ID NO 12
<211> LENGTH: 10
<212> TYPE: DNA
<213> ORGANISM: Artificial Sequence
<220> FEATURE:
<223> OTHER INFORMATION: Primer

<400> SEQUENCE: 12
gtccatgctg 10

<210> SEQ ID NO 13
<211> LENGTH: 5055
<212> TYPE: DNA
<213> ORGANISM: Artificial sequence
<220> FEATURE:
<223> OTHER INFORMATION: Nucleotide sequence of fMP 1035

<400> SEQUENCE: 13
gaattctaga tatttcagta ttgccatttt ctatagcgca gtgcaaaaga gaacacccat 60
attcattaat catattcggg tccgagtcat tgtcttttaa agctttaata acatcagaaa 120
cacagccaga ttcgatagcc tcaaatacct ccatgttgtg taatattagt agtatccgtg 180
tatgtacacc ggatgtacca agcgatataa aaatgattaa aatttcaatt tttatttaac 240
attaggatgt ctatttcata atcccgttat tagtagttag tggttagtaa gtaccatatt 300
actactaata agataaaaaa taaaactgct gatgtacagt ttatacccat aatgaaatta 360
tttataaaat cctcagccat ggaaataatg aaatgataca accaattcat atacaatgtt 420
tatttatagg atctattatg aattaatatt tttttacttt ttaactaaac gcgatttaat 480
aaatctacta tagtatcaat attatttcaa ataataaaaa aatattatac ggttagtaat 540
gtactttaat gtataccaaa ataaaatcta atagagtaat gtctttttaa tttcatatat 600
atcattagga tttatacatt taattgggta ttcagttcca taacctctat aattatcatc 660
agtagcctta aacatttctt ctttattaac atacttacat ttattggtat cgttcatgtt 720
agatttcaaa tcgtcagtat atactaaagg tgccattgcc aaacagaact cttcttggga 780
tagttcatct acataaaatt taccatcgct gtctaccata ccaagaaatt catttcttgt 840
agtatattgg atacatccag aaacatactc tatatcagaa tttaaacatc ctatgaatat 900
attcattata atacatgatg tcataaactt acatttagtg tcgtaatcga acacctttaa 960
tatcgattcc ggagtagttt tagttccatt tacctgcatg aataccatgc tatcagtaac 1020
tggagttact gtattaaagc atgatttgat ttcactactt atttcacgta gtataaccat 1080

-continued

```
tattgtaaag tgtagtagtt atatattatt ctgtaataag gaattaattt gctagttggg   1140
ttataaaacg ttctagataa atctattaat aattcatttt tatatatgtt actcggaaga   1200
aattactatt tactagttaa ttatagaata gataagtctt aataatttac ttttagtatt   1260
actcggaaga aattactata gttgactgta taaacattat aagaaagaat aaattcaaaa   1320
atatttataa aataaatatt ctaccatctt ccgtaaacat ctttatattc tgttactagg   1380
tattcttttc ctacatatct tacaggaaat tctctggcgt gtgtatcatt aagccaatat   1440
ctacaatatg gaatttcgac atggccgatg acactttcgt ttacctttat acttgtgtat   1500
ctgtaatcca ccacattttg tgtgaagccc tgcggtcttt cgtatgacat tacacctcct   1560
gttactatac cggttactct ccatctagga ttgccgtaat tacttcctac gaagcaagtt   1620
atcttggttt cgttttcatg tttttctagt agataggtta taccttcttt tttaatttcg   1680
atacatcttt gatacgtttc ctctttccca gaagcagtaa gtagtacaca ggtaaagcac   1740
aaactttgag gacctgtttt tttaactgta aaagtagaag tatctccact aacagttact   1800
tcatatatat ctctataagg actaggaaca taattgaaag cgttaagtcc gttacctcct   1860
acctgctctt gggctaccat aatcccatcg ctgcctctcc aagtagctct tgatattcct   1920
tctccgtatt cggttctgca ttgtaatttt acagggctac ccggtacacc ttcttctcca   1980
tagatatttt tcaagctaaa tgctattata gtaattgcta gaaataaata attagccttc   2040
atcttgattg ctttatatta aacactggat aatgtacgag gatcacatat agtagttaat   2100
atacttattc actttttaat taaaaatgta ttaatcttaa aaaaatatca aaaattaaac   2160
caaccacctc ttataacgag atttctgtcc aggttccatc aaagatgatc cagagatcag   2220
aaccacagaa aggtcctgta atttttcatc gtaagaagtc atagatgcta cataatctct   2280
acttagaccc aagtaactta ccgtaaatat tactgtagta gtacaatcag tgtaatttgt   2340
atttgctact atttttttac attcattatc tttcgaatat tctaccaata cttgaatatc   2400
ttcgttcaac ttcacaccac ctgctctaac atctactttt acttcgtggt cttctatagt   2460
tctagtccta tttattataa aatcaatcaa atctttatct acattatcta taacatacgc   2520
atctacgtga ggcattactc tgagttctat accgtgtctg taactctctg ttccgttgta   2580
atagaagata catctatagc gaccttcgtc atttctggat gaccttttag gaagttcaac   2640
attatattct ttaactggat cgttacaata gcatatactg tcttctccgg catcatgtat   2700
gtcaatagtt gccttaaacg cgttattttt catgtttcct tttactacaa tcagtttagt   2760
agcgtgtctg tcaggtggta gaagacaagt caaattaacc attacatcgt tatgtactac   2820
catagtataa gatcgacatt gtaggaaggt agccaataag aataaagaaa ctacgtacac   2880
ttttccagcc attatttttt ttaccaacta ctaataatgc tacactagtg ttagtgttat   2940
atttatgttt tttcctaata atatctggaa atcgttttaa gatcttccat agataaattt   3000
gacaatatta ctctatgtat ctcaggagat agtagacacc atctgctgct atgatcttta   3060
ctagcgtatt cattgatgat cgataacgtc aagtctatag ctgtcttcct tttttccatg   3120
tattttatat gcttcttaat aaaacaacga aatatcctta tatttttaag atctatcctt   3180
cgtatacgtt ttatagaatt agttagacca tccagtttat ctaatatcag aacatcgtac   3240
aaggatattt tcttatcacc cgtataaaat acattgtctt tcataatgga cagttcgtgt   3300
tctatttcat cctttaatgc tttggtttct ttatagttgt ttacaaatct catattacgt   3360
ataaaacctt gtttcttctt tatagaagag tcgtttatca cagaaaagta taaatatatt   3420
```

-continued

```
acagcaatga acacagcagg attattacgg gctttatgaa tagtgatggg agtatgaaat   3480

ctattcataa aacacatatc cgctccgtgt tctaacagta cgcgagtaca ttcttcacac   3540

ttattacgta tagcgtaagt tagtgctgta tttttatcat aatctgtttg attaacgtca   3600

gctccattag ctaataagta tttcatatta cttactttac tttctctaga acaaatcatt   3660

aaaggtgtta tcccgtaatt atctagtttc gttaacgtta gctccgtttt ttagtaatat   3720

ctttatatta ctaatcctag agtacataca ggctaaatgt ataggtgttt taccgtatct   3780

atttcttaca ttaacatcag cacctttatt aacaagtagt ctagtaagcc tagaagtatt   3840

tatagaaaca gccgcgtgta tagggtacat attacaagca tcgcatgata cgtttatatc   3900

ctttatcttc tttagcagtt ttcttgtaat aggtaaattc cttaattcgt atatacacat   3960

gcagagtata gaaataggta gataatgaat aggtaaacta agtatgtatg agataatact   4020

ataatacctc ttacatatcg cttccatcag tatatcgtta caacatctta tttgagctcc   4080

gtgtttaact agaatattga ataatcttac accgtgttta ctagacatta tagcgtattt   4140

taacattgta tatacatctc ctatatctgg atctgcgccg tggtttaata ataaatttac   4200

cagagtaaca ttttcttgtt ctacagcatg atataatgca gtatgcgtgt tttcgcatat   4260

acccgtgtta acatcaactc ctgcatcaat gaataacttt actattttag gactattagt   4320

tttaacggct tctaagaaat aatcttctaa cattgtatct gtatctacta ataaattatt   4380

agttataaaa tattctacta gttctgtatt tctagctcta attgcgcact taatagtaat   4440

gtttcgcata taatataaac ttggatgttt agtttcttcc catagaattt gacatagggg   4500

tatagtacta aaatatgaat atcctgtagc ataaccgttt ttaacacaat atgaactacc   4560

cttgtaagaa tctaatacgt aagatctaca cgccattttc aaatcagcgc catgttttat   4620

caaaagtttt agtatttctg tatatttttc tatattattt gcagatgtta gtagacgcct   4680

tattcttttt tcgggtttaa ccgttttatt atcattatat aacatcatcc taccccctgc   4740

taacactata gctatgttaa tgggatgaga ttttatagtt tcaccaccgt taataaccgc   4800

accgttacct aataacattt ttattatatc tatattcgaa tgttctatag caatatgtaa   4860

agcaagtagt ctattgctat cgtacataat tattatgtct ttatcttctt ctatcaatac   4920

acgaagcctg tctacattat tttcttttaa gatattatgt aatgatagca aacgatctgt   4980

agcgttgtgt ctgtaaacta gcttcatttt ttctggagtt atacaaagat acagtgattt   5040

ttaatatatg aattc                                                    5055
```

<210> SEQ ID NO 14
<211> LENGTH: 49
<212> TYPE: DNA
<213> ORGANISM: Artificial Sequence
<220> FEATURE:
<223> OTHER INFORMATION: oligonucleotide for construction of plasmid pGTPs

<400> SEQUENCE: 14

```
ccggaatcgc atgcggtacc cgggatccgc ggcccccccg gccgatatt                49
```

<210> SEQ ID NO 15
<211> LENGTH: 24
<212> TYPE: DNA
<213> ORGANISM: Artificial Sequence
<220> FEATURE:
<223> OTHER INFORMATION: oligonucleotide for construction of plasmid pGTPs

<400> SEQUENCE: 15

-continued agctgccccc ccggcaagct tgca 24

<210> SEQ ID NO 16
<211> LENGTH: 17
<212> TYPE: DNA
<213> ORGANISM: Artificial Sequence
<220> FEATURE:
<223> OTHER INFORMATION: oligonucleotide for construction of plasmid pGTPs

<400> SEQUENCE: 16
tcgacatttt tatgtac 17

<210> SEQ ID NO 17
<211> LENGTH: 22
<212> TYPE: DNA
<213> ORGANISM: Artificial Sequence
<220> FEATURE:
<223> OTHER INFORMATION: oligonucleotide for construction of plasmid pGTPs

<400> SEQUENCE: 17
aattcggccg ggggggccag ct 22

<210> SEQ ID NO 18
<211> LENGTH: 14
<212> TYPE: DNA
<213> ORGANISM: Artificial Sequence
<220> FEATURE:
<223> OTHER INFORMATION: oligonucleotide for construction of plasmid pGTPs

<400> SEQUENCE: 18
ggcccccccg gccg 14

<210> SEQ ID NO 19
<211> LENGTH: 28
<212> TYPE: DNA
<213> ORGANISM: Artificial Sequence
<220> FEATURE:
<223> OTHER INFORMATION: Primer

<400> SEQUENCE: 19
cgggatccat tgacatggct agcttgaa 28

<210> SEQ ID NO 20
<211> LENGTH: 26
<212> TYPE: DNA
<213> ORGANISM: Artificial Sequence
<220> FEATURE:
<223> OTHER INFORMATION: Primer

<400> SEQUENCE: 20
ttggtataaa agggagaaat ttctac 26

<210> SEQ ID NO 21
<211> LENGTH: 26
<212> TYPE: DNA
<213> ORGANISM: Artificial Sequence
<220> FEATURE:
<223> OTHER INFORMATION: Primer

<400> SEQUENCE: 21
aatttctccc ttttatacca aaaaca 26

-continued

<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
tgttgccaaa gaaatctgct attgc 25

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
tagcagattt ctttggcaac actc 24

<210> SEQ ID NO 24
<211> LENGTH: 28
<212> TYPE: DNA
<213> ORGANISM: Artificial Sequence
<220> FEATURE:
<223> OTHER INFORMATION: Primer

<400> SEQUENCE: 24
ccgctcgagt catgtgaata gtaatgtc 28

<210> SEQ ID NO 25
<211> LENGTH: 11
<212> TYPE: DNA
<213> ORGANISM: Artificial Sequence
<220> FEATURE:
<223> OTHER INFORMATION: oligonucleotide for construction of plasmid pNZ6929Sfi

<400> SEQUENCE: 25
gatccagcat g 11

<210> SEQ ID NO 26
<211> LENGTH: 10
<212> TYPE: DNA
<213> ORGANISM: Artificial Sequence
<220> FEATURE:
<223> OTHER INFORMATION: oligonucleotide for construction of plasmid pNZ6929Sfi

<400> SEQUENCE: 26
gtccatgctg 10

<210> SEQ ID NO 27
<211> LENGTH: 22
<212> TYPE: DNA
<213> ORGANISM: Artificial Sequence
<220> FEATURE:
<223> OTHER INFORMATION: Adaptor

<400> SEQUENCE: 27
aattcggccg gggggccag ct 22

<210> SEQ ID NO 28
<211> LENGTH: 14
<212> TYPE: DNA
<213> ORGANISM: Artificial Sequence
<220> FEATURE:

-continued

```
<223> OTHER INFORMATION: Adaptor

<400> SEQUENCE: 28

ggcccccccg gccg                                                    14
```